(12) United States Patent
Rogers

(10) Patent No.: US 9,587,238 B1
(45) Date of Patent: Mar. 7, 2017

(54) GENE-TARGETED APOPTOSIS

(71) Applicant: Yale University, New Haven, CT (US)

(72) Inventor: Faye A. Rogers, Norwalk, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 14/335,371

(22) Filed: Jul. 18, 2014

Related U.S. Application Data

(60) Provisional application No. 61/856,635, filed on Jul. 19, 2013.

(51) Int. Cl.
    *C07H 21/02*    (2006.01)
    *C07H 21/04*    (2006.01)
    *A61K 48/00*    (2006.01)
    *C12N 15/113*    (2010.01)

(52) U.S. Cl.
    CPC ........ *C12N 15/113* (2013.01); *C12N 2310/15* (2013.01)

(58) Field of Classification Search
    CPC ... A61K 48/00; C12N 2310/11; C12N 15/113
    See application file for complete search history.

(56) References Cited

U.S. PATENT DOCUMENTS 6,153,596 A * 11/2000 Liotta .................... C12N 15/88
    435/6.14
8,067,574 B2 * 11/2011 Hochberg .......... C12N 15/1135
    435/325
8,986,992 B2 * 3/2015 Peled ................... C12N 5/0647
    435/372

FOREIGN PATENT DOCUMENTS

WO    WO 93/09788 A1    5/1993

OTHER PUBLICATIONS

Slamon et al., Science, vol. 244, pp. 707-712, 1989.*
Frank-Kamenetskii et al., Triplex DNA structures. Annu Rev Biochem. 1995;64:65-95. Review.
Knauert et al., Triplex forming oligonucleotides: sequence-specific tools for gene targeting. Hum Mol Genet. Oct. 1, 2001;10(20):2243-51. Review.
Ziemba et al., A bis-alkylating triplex forming oligonucleotide inhibits intracellular reporter gene expression and prevents triplex unwinding due to helicase activity. Biochemistry. May 6, 2003;42(17):5013-24.

* cited by examiner

*Primary Examiner* — Amy Bowman
(74) *Attorney, Agent, or Firm* — Wolf, Greenfield & Sacks, P.C.

(57) ABSTRACT

Described herein are methods of triplex-induced apoptosis, in which multiple triplexes are formed in cells in which gene amplification has occurred (cells comprising/characterized by at least one amplified gene), referred to as target cells, and apoptosis is induced in the target cells.

14 Claims, 22 Drawing Sheets

FIG. 1
FIG. 1A
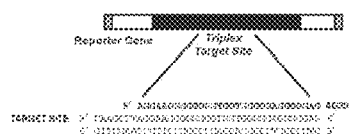
FIG. 1B
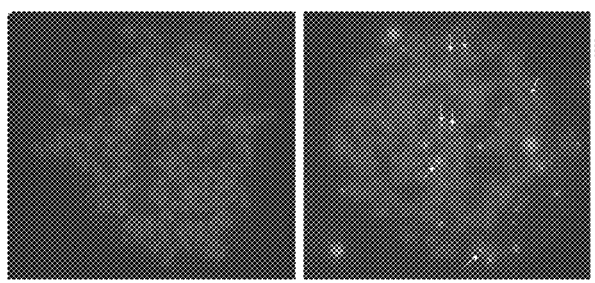
MIX30　　　　　AG30
FIG. 1C
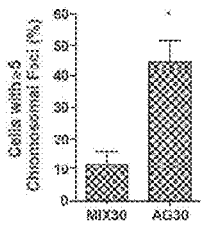
FIG. 1D
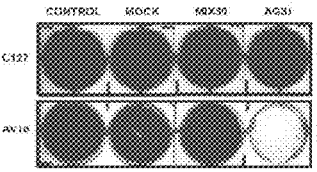
FIG. 1E
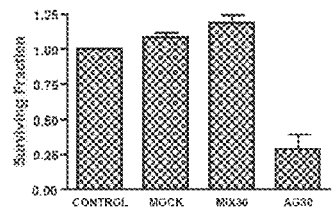
FIG. 1F
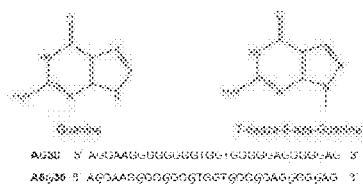
FIG. 1G
AG30　　　　　A8G30
FIG. 1H

FIG. 2
FIG. 2A
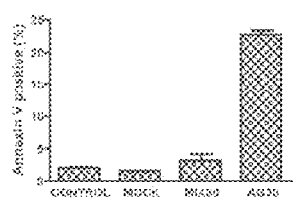
FIG. 2D
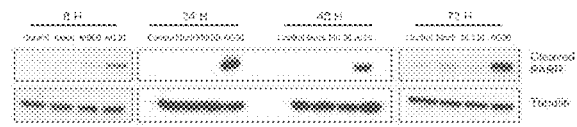
FIG. 2B
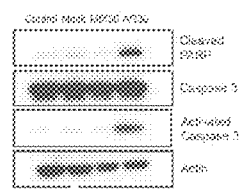
FIG. 2E
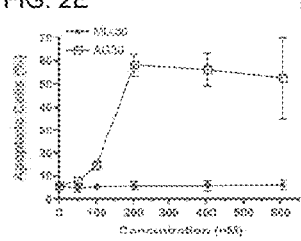
FIG. 2F
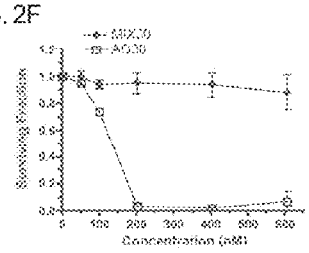
FIG. 2C
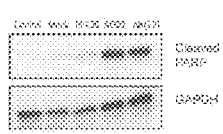

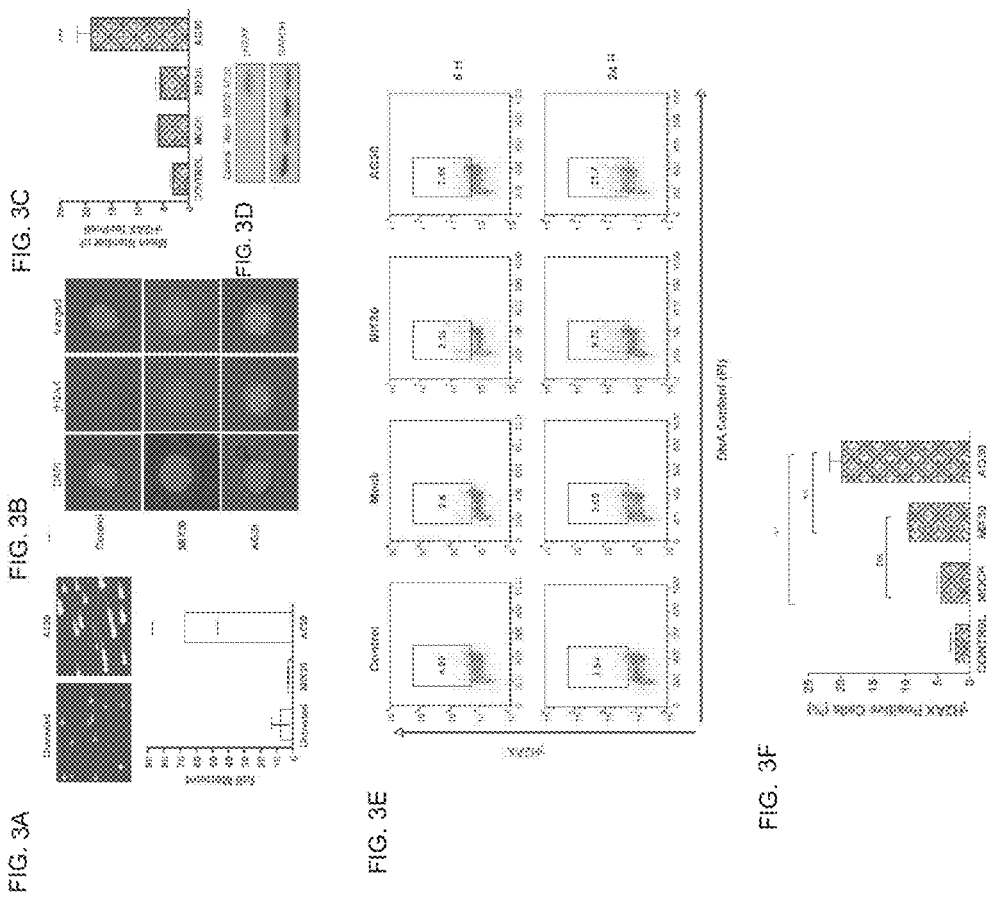

FIG. 4
FIG. 4A
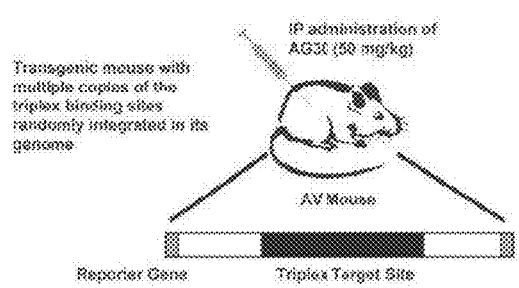
FIG. 4B
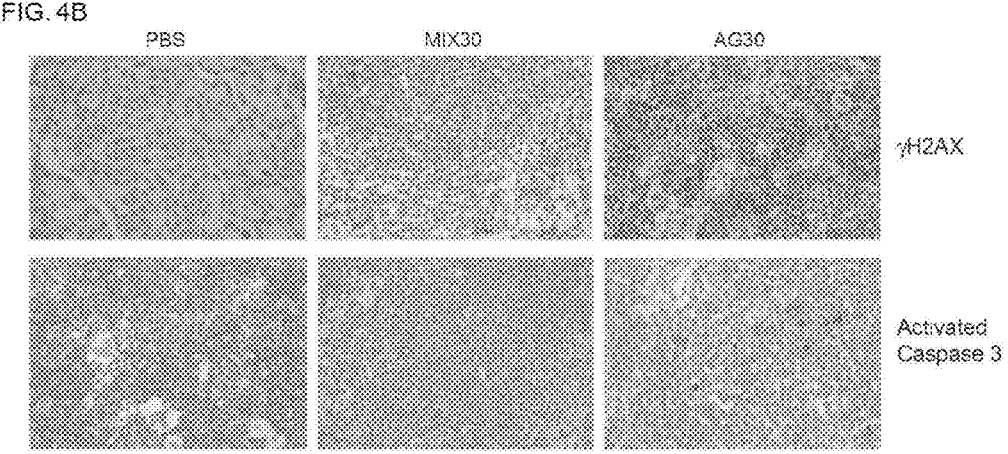
FIG. 4C
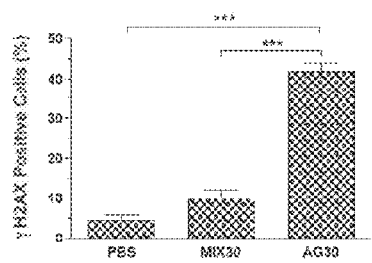
FIG. 4D
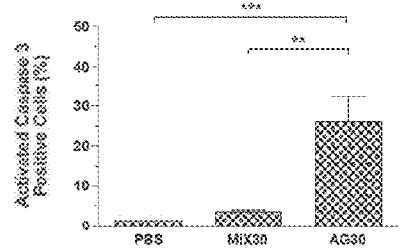

FIG. 5
FIG. 5A
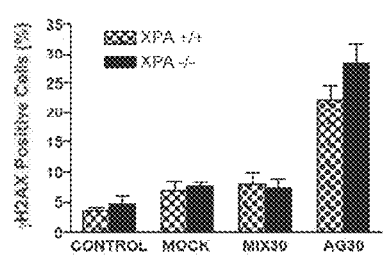
FIG. 5B
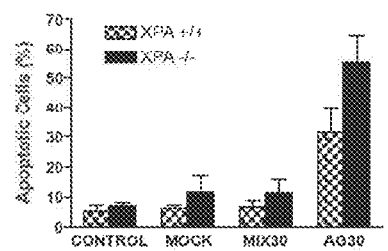
FIG. 5C
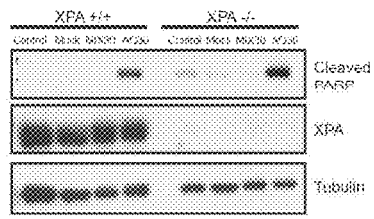

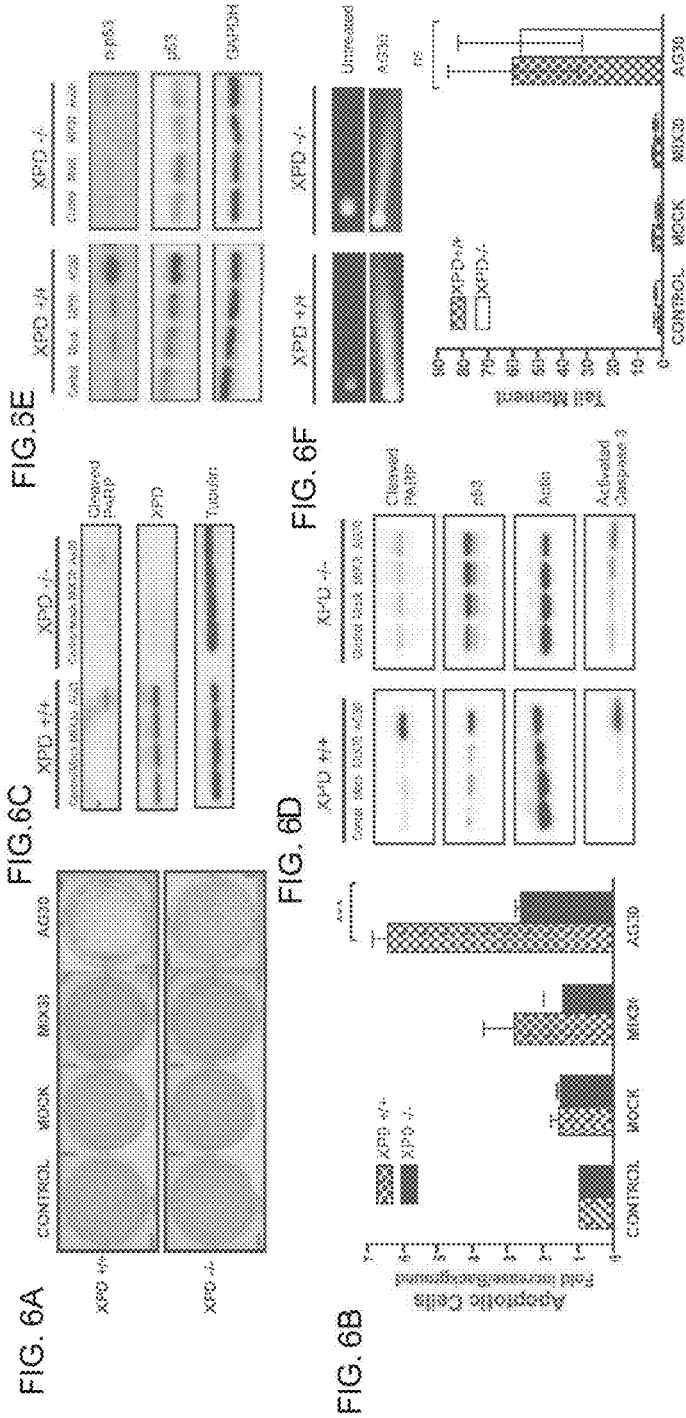

FIG. 7
FIG. 7A
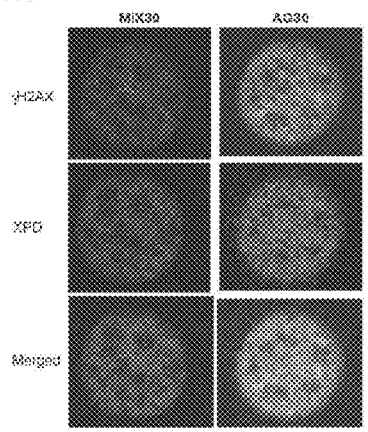
FIG. 7D
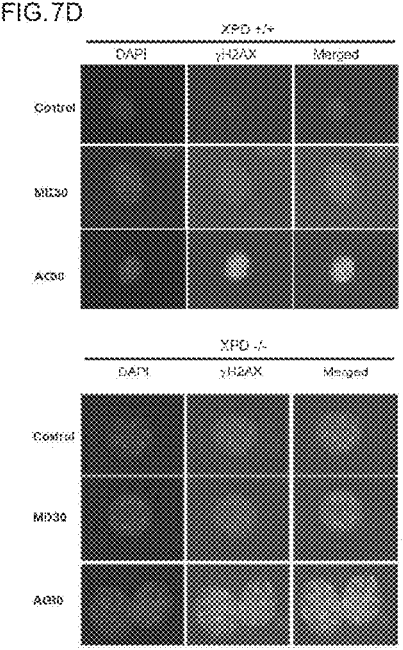
FIG. 7B
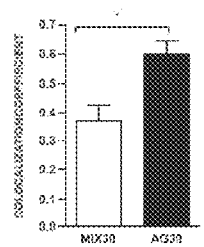
FIG. 7C
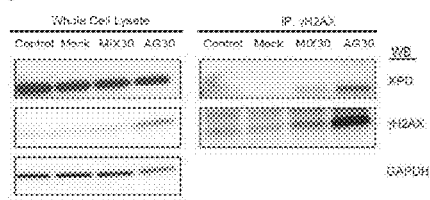
FIG. 7E
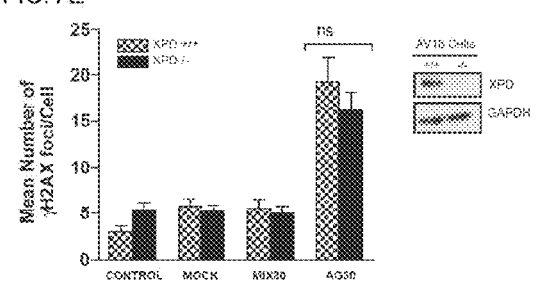

FIG. 8
FIG. 8A
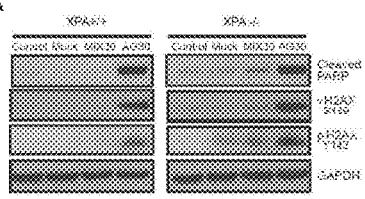
FIG. 8D
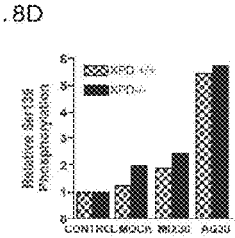
FIG. 8F
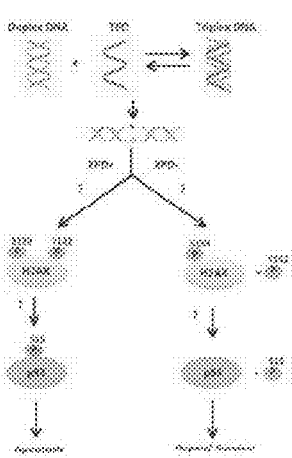
FIG. 8B
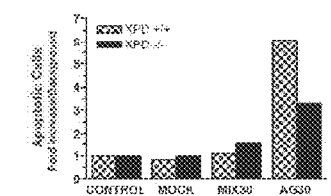
FIG. 8E
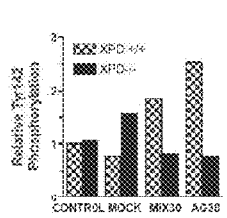
FIG. 8C
FIG. 8G
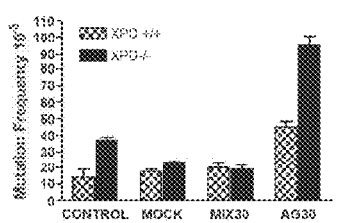

FIG. 9
FIG. 9A
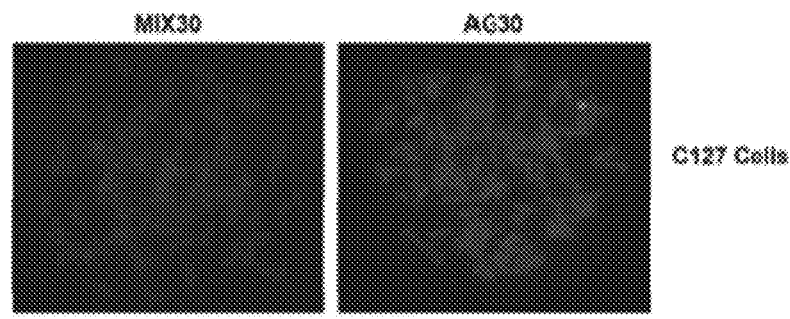
FIG. 9B
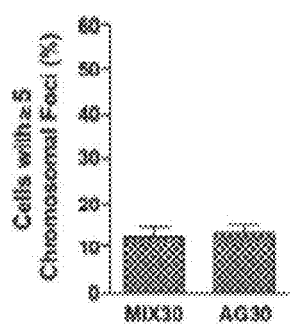

FIG. 10
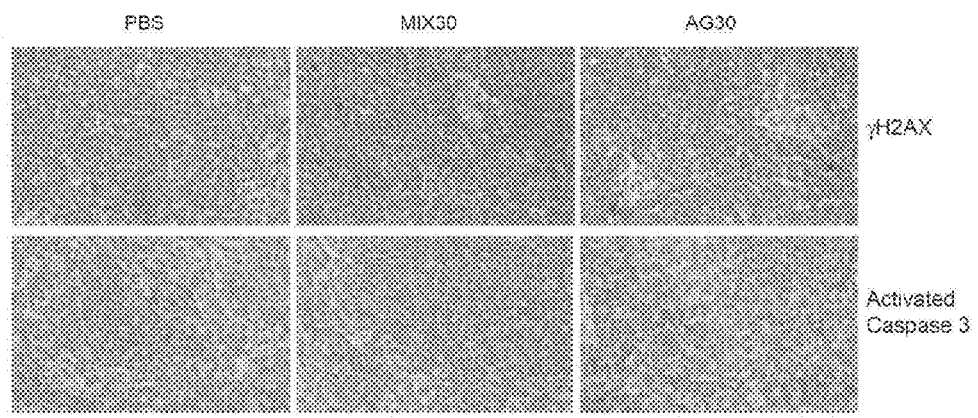
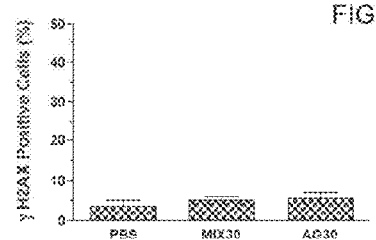 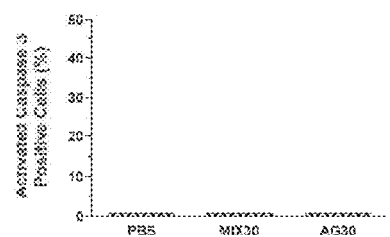

FIG. 14

```
                         SEQUENCE LISTING

<160> NUMBER OF SEQ ID NOS: 19

<210> SEQ ID NO 1
<211> LENGTH: 16
<212> TYPE: PRT
<213> ORGANISM: artificial sequence
<220> FEATURE:
<223> OTHER INFORMATION: synthetic polypeptide

<400> SEQUENCE: 1

Arg Gln Ile Lys Ile Trp Phe Gln Asn Arg Arg Met Lys Trp Lys Lys
1               5                   10                  15

<210> SEQ ID NO 2
<211> LENGTH: 18
<212> TYPE: PRT
<213> ORGANISM: artificial sequence
<220> FEATURE:
<223> OTHER INFORMATION: synthetic polypeptide

<400> SEQUENCE: 2

Pro Thr Asp Arg Gln Ile Lys Trp Phe Gln Asn Arg Arg Met Lys Trp
1               5                   10                  15

Lys Lys

<210> SEQ ID NO 3
<211> LENGTH: 11
<212> TYPE: PRT
<213> ORGANISM: artificial sequence
<220> FEATURE:
<223> OTHER INFORMATION: synthetic polypeptide

<400> SEQUENCE: 3

Tyr Gly Arg Lys Lys Arg Arg Gln Arg Arg Arg
1               5                   10

<210> SEQ ID NO 4
<211> LENGTH: 18
<212> TYPE: PRT
```

```
<213> ORGANISM: artificial sequence
<220> FEATURE:
<223> OTHER INFORMATION: synthetic polypeptide

<400> SEQUENCE: 4

Arg Gly Gly Arg Leu Ser Tyr Ser Arg Arg Phe Ser Thr Ser Thr
1               5                   10                  15

Gly Arg

<210> SEQ ID NO 5
<211> LENGTH: 10
<212> TYPE: PRT
<213> ORGANISM: artificial sequence
<220> FEATURE:
<223> OTHER INFORMATION: synthetic polypeptide

<400> SEQUENCE: 5

Arg Arg Leu Ser Tyr Ser Arg Arg Phe
1               5                   10

<210> SEQ ID NO 6
<211> LENGTH: 12
<212> TYPE: PRT
<213> ORGANISM: artificial sequence
<220> FEATURE:
<223> OTHER INFORMATION: synthetic polypeptide

<400> SEQUENCE: 6

Pro Ile Arg Arg Arg Lys Lys Leu Arg Arg Leu Lys
1               5                   10

<210> SEQ ID NO 7
<211> LENGTH: 12
<212> TYPE: PRT
<213> ORGANISM: artificial sequence
<220> FEATURE:
<223> OTHER INFORMATION: synthetic polypeptide

<400> SEQUENCE: 7

Arg Arg Gln Arg Arg Thr Ser Lys Leu Met Lys Arg
1               5                   10

<210> SEQ ID NO 8
<211> LENGTH: 15
<212> TYPE: PRT
<213> ORGANISM: artificial sequence
<220> FEATURE:
<223> OTHER INFORMATION: synthetic polypeptide

<400> SEQUENCE: 8

Arg Arg Arg Arg Asn Arg Thr Arg Arg Asn Arg Arg Arg Val Arg
1               5                   10                  15

<210> SEQ ID NO 9
<211> LENGTH: 19
<212> TYPE: PRT
<213> ORGANISM: artificial sequence
<220> FEATURE:
<223> OTHER INFORMATION: synthetic polypeptide

<400> SEQUENCE: 9

Lys Met Thr Arg Ala Gln Arg Arg Ala Ala Ala Arg Arg Asn Arg Trp
1               5                   10                  15

Thr Ala Arg
```

```
<210> SEQ ID NO 10
<211> LENGTH: 13
<212> TYPE: PRT
<213> ORGANISM: artificial sequence
<220> FEATURE:
<223> OTHER INFORMATION: synthetic polypeptide

<400> SEQUENCE: 10

Thr Arg Arg Gln Arg Thr Arg Arg Ala Arg Arg Asn Arg
1               5                   10

<210> SEQ ID NO 11
<211> LENGTH: 13
<212> TYPE: PRT
<213> ORGANISM: artificial sequence
<220> FEATURE:
<223> OTHER INFORMATION: synthetic polypeptide

<400> SEQUENCE: 11

Gly Arg Lys Lys Arg Arg Gln Arg Arg Arg Pro Pro Gln
1               5                   10

<210> SEQ ID NO 12
<211> LENGTH: 13
<212> TYPE: PRT
<213> ORGANISM: artificial sequence
<220> FEATURE:
<223> OTHER INFORMATION: synthetic polypeptide

<400> SEQUENCE: 12

Gly Arg Arg Arg Arg Arg Arg Arg Arg Arg Pro Pro Gln
1               5                   10

<210> SEQ ID NO 13
<211> LENGTH: 30
<212> TYPE: DNA
<213> ORGANISM: artificial sequence
<220> FEATURE:
<223> OTHER INFORMATION: synthetic polynucleotide

<400> SEQUENCE: 13
aggaaggggg gggtggtggg ggaggggag                                    30

<210> SEQ ID NO 14
<211> LENGTH: 30
<212> TYPE: DNA
<213> ORGANISM: artificial sequence
<220> FEATURE:
<223> OTHER INFORMATION: synthetic polynucleotide

<400> SEQUENCE: 14
agtcagtcag tcagtcagtc agtcagtcag                                    30

<210> SEQ ID NO 15
<211> LENGTH: 28
<212> TYPE: DNA
<213> ORGANISM: artificial sequence
<220> FEATURE:
<223> OTHER INFORMATION: synthetic polynucleotide

<400> SEQUENCE: 15
gggaggagga ggtggaggag gaagagga                                      28

<210> SEQ ID NO 16
<211> LENGTH: 24
<212> TYPE: DNA
<213> ORGANISM: artificial sequence
```

```
<220> FEATURE:
<223> OTHER INFORMATION: synthetic polynucleotide

<400> SEQUENCE: 16
gaggaggagt gggagaatgg gggg                                              24

<210> SEQ ID NO 17
<211> LENGTH: 37
<212> TYPE: DNA
<213> ORGANISM: artificial sequence
<220> FEATURE:
<223> OTHER INFORMATION: synthetic polynucleotide

<400> SEQUENCE: 17 gaggggagg gggtggtggg gggggaagga ttcgaac                                 37

<210> SEQ ID NO 18
<211> LENGTH: 37
<212> TYPE: DNA
<213> ORGANISM: artificial sequence
<220> FEATURE:
<223> OTHER INFORMATION: synthetic polynucleotide

<400> SEQUENCE: 18
gttcgaatcc ttcccccccc accacccccct ccccctc                               37

<210> SEQ ID NO 19
<211> LENGTH: 30
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (2)..(2)
<223> OTHER INFORMATION: n is 7-deaza-8aza-guanine
<220> FEATURE:
<221> NAME/KEY: misc_feature
<222> LOCATION: (7)..(7)
<223> OTHER INFORMATION: n is 7-deaza-8aza-guanine
<220> FEATURE:
<221> NAME/KEY: misc_feature
<222> LOCATION: (10)..(10)
<223> OTHER INFORMATION: n is 7-deaza-8aza-guanine
<220> FEATURE:
<221> NAME/KEY: misc_feature
<222> LOCATION: (13)..(13)
<223> OTHER INFORMATION: n is 7-deaza-8aza-guanine
<220> FEATURE:
<221> NAME/KEY: misc_feature
<222> LOCATION: (18)..(18)
<223> OTHER INFORMATION: n is 7-deaza-8aza-guanine
<220> FEATURE:
<221> NAME/KEY: misc_feature
<222> LOCATION: (21)..(21)
<223> OTHER INFORMATION: n is 7-deaza-8aza-guanine
<220> FEATURE:
<221> NAME/KEY: misc_feature
<222> LOCATION: (25)..(25)
<223> OTHER INFORMATION: n is 7-deaza-8aza-guanine
<220> FEATURE:
<221> NAME/KEY: misc_feature
<222> LOCATION: (28)..(28)
<223> OTHER INFORMATION: n is 7-deaza-8aza-guanine

<400> SEQUENCE: 19
angaagnggn ggntggtngg ngagnggnag                                        30
```

Gene-Targeted Apoptosis in HER2 Positive Breast Cancer Cell lines
FIG. 14A
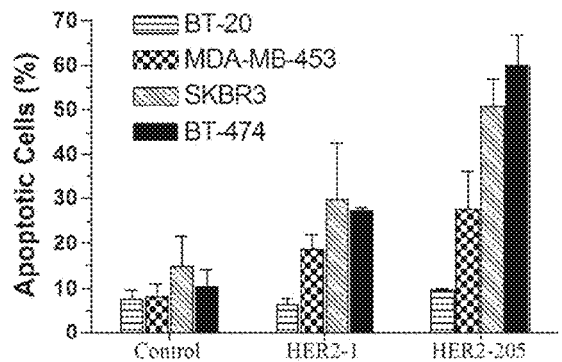
FIG. 14B
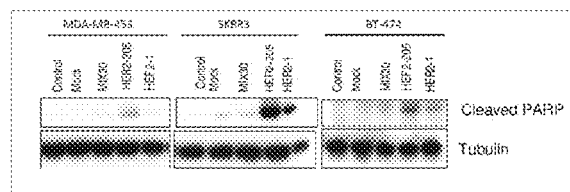

FIG. 15
Gene-Targeted Apoptosis Increases with HER2 Gene Copy Number
FIG. 15A
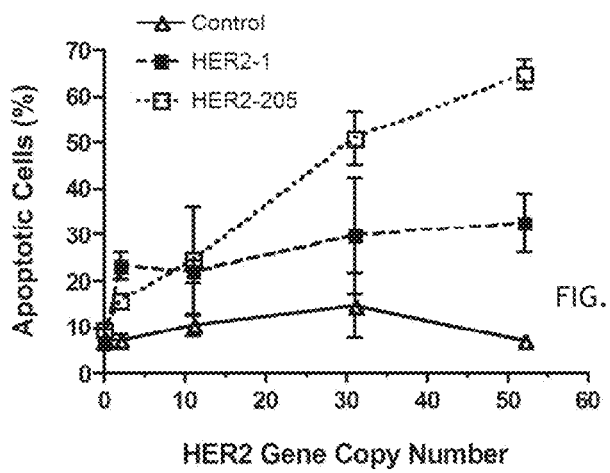
FIG. 15B
| Breast Cancer Cell Lines | HER2 Gene Copy Number |
|---|---|
| BT-20 | null |
| MCF7 | 2 |
| MDA-MB-453 | 11 |
| SKBR3 | 31 |
| BT474 | 52 |
FIG. 15C
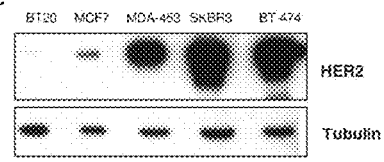

Dose Response of Triplex Induced Apoptosis in
HER2-Positive Breast Cancer Cells

FIG. 17
Triplex Structures Induce DSBs As Measured by Neutral Comet Assay
FIG. 17A
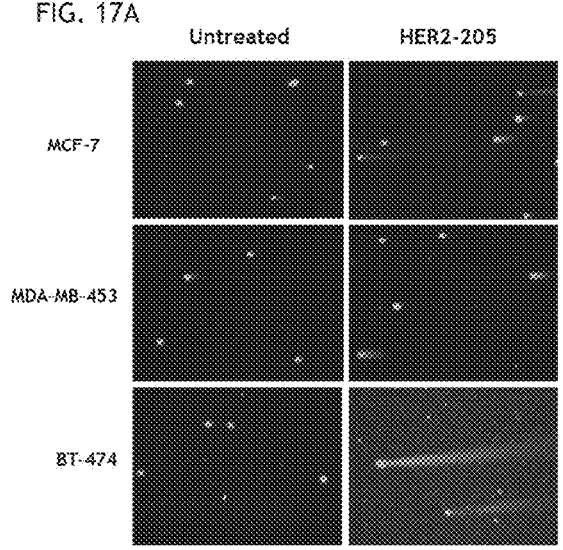
FIG. 17B
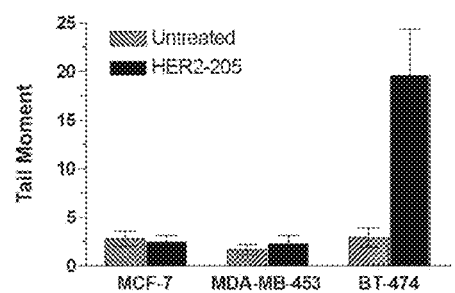

HER2-Targeted TFOs Induce γH2AX Foci In HER2 Overexpressing Breast Cancer Cells

Triplex-Induced γH2AX is Cell Cycle Independent

FIG. 20
Effect of Triplex Induced Apoptosis on Tumor Growth
*Pilot Study*
FIG. 20A
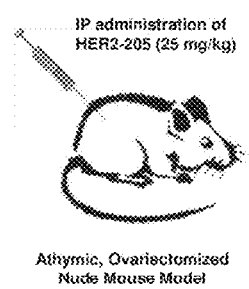
- Day 1: Implant estradiol pellet
- Day 3: Tumor inoculation with BT474 cells
- Day 28: Treatment
FIG. 20B
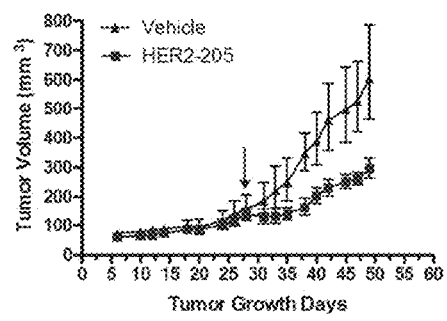

Triplex-Induced Apoptosis in HER2 Overexpressing Ovarian Cancer Cell Lines

Potential Treatment for Herceptin-Resistant Breast Cancers

Drug Design Strategy: Utilize agents that target HER2 positive breast cancers using mechanisms of actions independent of HER2 cellular growth function.

GENE-TARGETED APOPTOSIS

This invention was made with government support under CA120049 awarded by National Institutes of Health. The government has certain rights in the invention.

BACKGROUND

An intricate balance between DNA repair and apoptosis pathways has evolved in order to protect the integrity of the human genome against the potentially devastating effects of endogenous and exogenous genotoxins. Decisions to activate either pathway in response to DNA damage minimize the likelihood of genomic instability, which can lead to mutagenesis and ultimately to carcinogenesis.

SUMMARY

HER2 is a key player in a complex signaling network. As such, when deregulated, it becomes the major driver in sustaining the cancer phenotype in a biologically distinct subset of breast cancers. Hence, determination of HER2 status has become a routine prognostic and predictive factor in breast cancer treatment. In an effort to capitalize upon this therapeutic target, several drugs have been developed to block the HER2 pathway; most of these are aimed at the receptor, including the anti-HER2 antibody, Herceptin. Although Herceptin has improved the clinical outlook of HER2-positive breast cancer patients, there still remains a dire need for new therapeutics to treat cancers that have acquired Herceptin resistance. Research has suggested that Herceptin-resistance can be attributed in part to the activation of aberrant signaling pathways that compensate for the inhibition of HER2 cellular growth activity. Targeted drugs that utilize a mechanism of action that is independent of HER2 cellular function may avoid this form of acquired resistance.

Described herein is a method of triplex-induced apoptosis, in which multiple triplexes are formed in cells, referred to as target cells, in which gene amplification has occurred (cells comprising at least one amplified gene) and apoptosis is induced in the target cells. The method is useful for selectively inducing apoptosis in cells it is desirable to kill, such as cancer cells or other abnormal cells in which gene amplification has occurred (cancer or other abnormal cells which comprise at least one amplified gene); the effect on other cells (non-cancer or normal cells, which have only two copies of the corresponding gene/only two potential binding sites) is minimal. The method comprises introducing into target cells triplex-forming molecules (TFMs), such as DNA, triplex forming oligonucleotides (TFOs), peptide nucleic acids (PNA), oligos with non-natural bases or other modified oligonucleotides, in sufficient quantity to produce multiple apoptosis-inducing triplexes in the target cells and induce apoptosis. Triplex-forming molecules (TFMs) specifically recognize polypurine sites. Apoptosis is induced in response to formation of multiple triplex structures, not just one or two. The nucleotide excision repair (NER) pathway is capable of efficiently repairing a low level of damage and the extent to which triplexes are formed in the present method exceeds the cell's ability to repair DNA damage, with the result that apoptosis occurs. One embodiment is a method of inducing apoptosis in cancer cells, such as cancer cells in an individual (e.g. a human), by introducing sufficient TFOs into cancer cells to cause apoptosis. As described further below, this is done by contacting target cells with TFMs, such as TFOs, under conditions under which sufficient TFMs, such as TFOs, enter target cells and bind to a specific polypurine site(s), referred to as a target site. A particular advantage of the method is that TFMs, such as TFOs, used are "active" (bind their target sites, particularly target polypurine sites) in target cells (e.g., cancer cells or other abnormal cells which comprise at least one amplified gene) and not in healthy cells, thus avoiding adverse effects on healthy cells often seen when presently-used drugs are administered. Compositions described herein comprise TFMs, such as TFOs, that bind to their target (such as HER2) polypurine sites, form triplex structures and specifically activate apoptosis in the target cells, such as cancer cells in which gene amplification has occurred.

In a specific embodiment, the type of cancer is one in which the HER2 gene is amplified. HER2 gene amplification is seen in approximately 30% of breast cancers and also in ovarian cancer. Examples of other cancers in which gene amplification has occurred (and the associated amplified gene or genes) are included in the TABLE. For each of these as well and similar to the approach described for cancers in which HER2 is amplified, TFMs, such as TFOs, that bind to their target sites (one or more polypurine sites), form triplex structures and specifically activate apoptosis can be introduced into the cancer cells in sufficient quantity to induce apoptosis. Much of the description herein makes reference to TFOs, but it is to be understood that TFMs other than TFOs can be used as described. Gene amplification means that TFOs can be used to create multiple apoptosis-inducing triplexes specifically in the cancer cells; this does not occur in healthy cells, which lack amplification (e.g., lack HER2 amplification or amplification of one or more of the genes in the TABLE). The ability to create multiple triplexes in such cancer cells is enhanced by the occurrence of multiple polypurine sites, such as the multiple polypurine sites in the HER2 gene, which are highly amenable to triplex formation.

A specific embodiment described herein is an alternative and novel method to specifically target HER2-positive breast cancers and induce apoptosis by exploiting unique aspects of the genome of malignant cells: HER2 gene amplification. Also described herein are new anti-HER2 therapies with a novel mechanism of action. Notably, the method and compositions described herein are effective in cells that have become resistant to Herceptin and, thus, avoid limitations of presently-used therapies. They induce apoptosis in Herceptin-resistant cells and are useful for the treatment of primary and metastatic HER2-positive breast cancer. A particular advantage is that they overcome the acquired drug resistance that limits the efficacy of currently-used HER2-targeted therapies.

Also described herein are TFOs useful to selectively induce apoptosis in targeted cells. TFOs are designed such that they cause gene-targeted apoptosis in the cells and inhibit growth and metastasis of cells in which the causative/responsible gene occurs. In alternative embodiments, TFMs such as PNAs, oligos with non-natural bases or other modified oligonucleotides are used. The gene can be, for example, an amplified gene (e.g., HER2 or other amplified cancer gene, including those in the TABLE). TFOs are introduced into cells in which they are to act in sufficient quantity/concentration to trigger apoptosis. The TFOs can be introduced by a variety of methods, such as through modification of the oligonucleotide backbone or the use of a carrier or transport agent, which can be attached (covalently or non-covalently) to the TFO or mixed with (and not attached or conjugated to) TFOs. For example, hydrophobic molecules, such as lipids, (e.g., cationic lipids), cell-penetrating peptides (CPP) and cell-targeting ligands can be used to enhance the ability of TFOs to enter cells/improve their interaction with the cell membrane lipid (hydrophobic) bi-layer. In specific embodiments, cell-penetrating peptides (also known as protein transduction domains (PTDs), membrane translocating sequences (MTSs), and Trojan peptides) are used to enhance/facilitate uptake of TFOs into cells. CPPs are short peptides (about 40 amino acids or less) that are cationic, able to enter many cell types, and typically made up of mostly hydrophilic amino acids/rich in arginine and lysine. They have been shown to be able to carry many types of entities, including oligonucleotides, into cells. Hydrophilic CPPs include, but are not limited to: Penetratin or Antenapedia (RQIKIWFQNRRMKWKK (SEQ ID NO: 1) or alternatively, PTD RQIKWFQNRRMKWKK (SEQ ID NO: 2)); HIV TAT protein (YGRKKRRQRRR (SEQ ID NO: 3)); SynB1 (RGGRLSYSRRRFSTSTGR (SEQ ID NO: 4)); SynB3 (RRLSYSRRRF (SEQ ID NO: 5)); PTD-4 (PIRRRKKLRRLK (SEQ ID NO: 6)); PTD-5 (RRQRRTSKLMKR (SEQ ID NO: 7)); FHV Coat-(35-49) (RRRRNRTRRNRRRVR (SEQ ID NO: 8)); BMV Gag-(7-25) (KMTRAQRRAAARRNRWTAR (SEQ ID NO: 9)); HTLV-II Rex-(4-16) (TRRQRTRRARRNR (SEQ ID NO: 10)); D-Tat (GRKKRRQRRRPPQ (SEQ ID NO: 11)); and R9-Tat (GRRRRRRRRRPPQ (SEQ ID NO: 12)). Such CPPs can be covalently or non-covalently linked to TFMs, such as TFOs, or not linked to TFMs, such as TFOs; in the latter case, TFMs (TFOs) and CPPs are unconjugated when administered. In both embodiments, a sufficient quantity of TFMs (TFOs) and CPPs is administered to result in formation of multiple triplexes and induce apoptosis in the target cells. In the cells, TFMs, such as TFOs, bind their target sites.

In a specific embodiment, all or a fragment of Antennapedia peptide (the homeodomain of the *Drosophila* homeoprotein Antennapedia (residues 43-58), commonly named penetratin, (RQIKIWFQNRRMKWKK; Arg Gln Ile Lys IleTrp Phe Gln Asn Arg Arg Met Lys Trp LysLys) is used as a transport peptide to enhance uptake of TFOs (e.g., TFOs that target HER2, such as the TFO designated AG30 herein). Alternative sequence of Antennapedia peptide is PTD RQIKWFQNRRMKWKK (SEQ ID NO: 2). As shown in FIG. 1, TFO AG30 has the following sequence: 5'AGGAAGGGGGGGGTGGTGGGGGAGGGGGAG (SEQ ID NO: 13). The TFO and transport peptide are combined, such as by mixing together, and contacted with cells (such as mammalian, including human or rodent/mouse cells) into which they are to be introduced, under conditions under which entry into the cells occurs in sufficient quantity to produce multiple apoptosis-inducing triplexes in the target cells and induce apoptosis. Alternatively, the transport peptide (e.g., all or a fragment of Antennapedia peptide) is conjugated/attached, either covalently or non-covalently to TFOs to produce carrier/transport peptide-TFO complexes, which are contacted with cells into which they are to be introduced, under conditions under which they enter the cells in sufficient quantity to produce multiple apoptosis-inducing triplexes and induce apoptosis. In certain embodiments, the carrier or transport peptide amino acid sequence is modified from that presented herein, such as by adding one or more terminal lysine(s) to increase the (+) charge (increase the cationic nature), so that it will form a micelle that enhances uptake into the cell of the TFOs. For example, the Antennapedia peptide is modified by the addition of one or more terminal lysine(s), to make the peptide more cationic and able to form micelles.

TFOs and carrier peptides are administered to individuals who have cancer characterized by gene amplification (e.g., breast cancer in which HER2 gene amplification has occurred or any other cancer in which cancer gene amplification has occurred, such as those listed herein) by known methods, such as intravenous, intraperitoneal or other route of injection. In one embodiment, TFOs and carrier peptides are mixed together and administered in sufficient quantity and number of doses to have the desired effect of inducing apoptosis of cancer cells. In an alternative embodiment, TFO is joined, covalently or non-covalently, with an appropriate transport or carrier peptide is administered in sufficient quantity and number of doses to have the desired effect of inducing apoptosis of cancer cells.

Presented below is a TABLE that lists human cancers in which genes are amplified and the amplified gene. The present methods and compositions are appropriate for inducing apoptosis in these human cancers and others in which oncogene amplification has occurred.

The details of one or more embodiments of the disclosure are set forth in the description below. Other features or advantages of the present disclosure will be apparent from the following drawings and detailed description of several embodiments, and also from the appended claims.

BRIEF DESCRIPTION OF THE DRAWINGS

The following drawings form part of the present specification and are included to further demonstrate certain aspects of the presence disclosure, which can be better understood by reference to one or more of these drawings in combination with the detailed description of specific embodiments presented herein.

FIGS. 1A-1H. Analysis of triplex induced cell death. (FIG. 1A) Schematic for the generation of synthetic triplex DNA structures. Triplex structures were created using a 30mer TFO, AG30, which has been shown to bind sequence-specifically to the polypurine target sequence. The sequences, from top to bottom, correspond to SEQ ID Nos: 13, 17 and 18. (FIG. 1B) Images of a non-denatured metaphase chromosome spread generated from AV16 cells treated with either 2 µg of rhodamine-labeled AG30 or the control oligonucleotide, MIX30. (FIG. 1C) Quantification of AG30-induced chromosomal foci. 50-60 metaphase chromosome spreads were analyzed per treatment. *p<0.05. (FIG. 1D) The established mouse cell line (AV16) was engineered to contain randomly integrated chromosomal triplex target sites. Cells were treated with 2 µg of TFO and stained with crystal violet 48 h post-treatment. Monolayer growth assays demonstrate a decrease in cell survival that is proportional to an increase in triplex formation. (FIG. 1E) Survival by colony formation of AV16 cells following TFO-treatment [Mean±SEM, n=3]. (FIG. 1F) Structure of the natural guanine base compared to the modified base 7-deaza-8aza-guanine (PPG). Sequence of the PPG-substituted 30-mer TFO, A8G30 (SEQ ID NO: 19) compared to AG30 (SEQ ID NO: 13). G represents PPG. (FIG. 1G) Gel mobility shift assay of triplex formation. The target duplex was end-labeled and incubated with increasing concentrations of the indicated TFO followed by native polyacrylamide gel electrophoresis. (FIG. 1H) Monolayer growth assay reveal similar reduction in cell growth following treatment with either 2 µg of AG30 or A8G30.

FIG. 2. Induction of apoptosis via formation of triplex structures in AV16 cells. (FIG. 2A) Annexin-V binding to exposed phosphatidylserine residues 24 h after treatment with 2 µg of oligonucleotides. (FIG. 2B) Western blot analysis of caspase mediated cleavage of PARP. Cells were collected and lysates prepared 24 h post-treatment. (FIG.

2C) Activation of apoptosis can be attributed to triplex formation rather than G-quadruplex formation as determined by Western blot analysis of cleaved PARP following 2 μg treatment with AG30 or A8G30. (FIG. 2D) Time course of induced apoptosis by Western blot analysis of cleaved PARP. (FIG. 2E) Dose response of increasing concentrations of AG30 and its effect on apoptotic cell death 48 h post-treatment. (FIG. 2F) Clonogenic survival after 48 h-exposure of AV16 cells to AG30 or MIX30.

FIG. 3. Triplex formation induces DSBs. (FIG. 3A) Neutral single cell comet assay of untreated and AG30-treated AV16 cells and measurement of comet tail moment 24 h post-treatment. 100-150 cells were evaluated per treatment [Mean±SEM]. (FIG. 3B) Immunofluorescence of triplex-induced γH2AX foci 24 h post-treatment with MIX30 or AG30. (FIG. 3C) Quantification of γH2AX immunofluorescence. *p<0.001 (FIG. 3D) Western blot analysis of γH2AX protein levels 24 h post TFO-treatment. (FIG. 3E) Flow cytometry profiles of AV16 cells stained for expression of γH2AX and propidium iodide (PI) to measure DNA content and identify phases of the cell cycle. Cells were harvested 6 h and 24 h after treatment. The box indicates the gate for high levels of γH2AX and numbers represent percentage of cells with high levels of γH2AX. (FIG. 3F) Increase in the percentage of γH2AX positive cells 24 h following treatment with AG30. Data represents three independent experiments. p<0.01, ns=not significant.

FIG. 4. Triplex formation induced DSBs in transgenic mouse model. (FIG. 4A) Schematic of transgenic mouse model, AV, which contains ~50 copies of the triplex target site chromosomally integrated into its genome. (FIG. 4B) Immunohistochemistry of spleen samples harvested from AV mice 6 h post-treatment with MIX30 or AG30 (50 mg/kg). (FIGS. 4C and 4D) Quantitation of immunohistochemical findings. *p<0.001, p<0.01.

FIG. 5. Role of XPA in the activation of triplex-induced apoptosis. (FIG. 5A) Analysis of γH2AX expression levels as a measure of triplex-induced DSBs in XPA-proficient and XPA-deficient cells 24 hrs post AG30-treatment. (FIG. 5B) Detection of Annexin-V binding indicates an increase in apoptotic cell death in the absence of XPA 24 hrs post treatment with 2 μg of oligonucleotides. (FIG. 5C) Western blot analysis of caspase mediated cleavage of PARP as a measure of triplex-induced apoptosis.

FIG. 6. XPD is required for triplex-induced apoptosis. (FIG. 6A) Monolayer growth studies demonstate that XPD-deficient cells are resistant to triplex-induced decrease in cell growth. (FIG. 6B) Knockdown of XPD results in significant reduction of induced-apoptosis as measured by Annexin V staining. (***p<0.001) (FIG. 6C) Western blot analysis of activation of apoptosis as measured by cleaved PARP following siRNA knockdown of XPD. (FIG. 6D) Western blot analysis of triplex-induced apoptosis and effect on p53 levels. (FIG. 6E) Phosphorylation of p53 at serine 15 is reduced in XPD-knockdown cells in the presence of multiple triplex structures. (FIG. 6F) Neutral single cell comet assay of untreated and AG30 treated XPD-proficient and deficient cells. Measurement of comet tail moment 24 h after treatment reveals similar levels of DSBs. 100-150 cells were evaluated per treatment [Mean±SEM], ns=not significant.

FIG. 7. XPD is recruited to the γH2AX site. (FIG. 7A) Confocal microscopy indicates co-localization of XPD with γH2AX foci. (FIG. 7B) Co-localization coefficient calculated using NIH ImageJ software (*p<0.05). (FIG. 7C) Co-immunoprecipitation of γH2AX with XPD by western blot analysis. (FIG. 7D) Immunofluorescence studies of γH2AX foci formation in XPD+/+ and XPD−/− cells 24 h post AG30 treatment. (FIG. 7E) Western blot analysis of XPD protein levels in proficient and deficient cells. Quantification of γH2AX foci formation per cell. 60-70 cells were evaluated per treatment.

FIG. 8. Activation of apoptosis minimizes triplex-induced genomic instability. (FIG. 8A) Western blot analysis of H2AX phosphorylation at serine139 and tyrosine142 in XPA-proficient and deficient cells 24 hrs following AG30 treatment. (FIG. 8B) Analysis of triplex-induced apoptosis in XPD+/+ and XPD−/− cells as measured by Annexin-V staining. (FIG. 8C) Western blot analysis of the phoshorylation status of H2AX at serine 139 and tyrosine 142 in XPD-proficient and deficient cell 24 h following TFO treatment. (FIGS. 8D and 8E) Quantification of the relative S139 and Y142 phosphorylation levels in XPD-deficient cells compared to XPD-proficient cells in response to triplex-induced DNA double strand breaks. (FIG. 8F) Schematic of XPD-dependent triplex-induced apoptosis. (FIG. 8G) Triplex-induced genomic instability as determined by mutation frequencies in the supFG1 reporter gene in XPD+/+ and XPD−/− cells treated with TFOs. The frequency of mutations was calculated by dividing the number of colorless mutant plaques by the total number of plaques counted. Each experiment was performed in triplicate and the standard errors were calculated for the mutation frequency. [Mean±SEM, n=3]

FIG. 9. Treatment of the parental cell line (C127), which lacks the polypurine/polypyrimidine target site (FIG. 9A), with rhodamine-AG30 further confirms the specificity of third strand binding (FIG. 9B).

FIG. 10. Immunohistochemistry analysis of spleen tissue (FIG. 10A) revealed no increase in the percentage of cells positive of γH2AX foci above background (FIG. 10B, FIG. 10C).

FIG. 12.

FIG. 14. Gene-targeted apoptosis in HER2 positive breast cancer cell lines. (FIG. 14A) Annexin-V binding to exposed phosphatidylserine residues 24 h after treatment with 2 ug of HER2-targeted TFOs, HER2-1 and HER2-205. (FIG. 14B) Western blot analysis of caspase mediated cleavage of PARP as a measure of triplex-induced apoptosis.

FIG. 15. Gene-targeted apoptosis increases with an increase in HER2 gene copy number. (FIG. 15A) Analysis of triplex-induced apoptosis in several breast cancer cell lines treated with HER2-1 or HER2-205. Detection of Annexin-V binding indicates an increase in apoptotic cell death that corresponds with an increase in gene copy number. (FIG. 15B) HER2 gene copy number in several breast cancer cells lines. (FIG. 15C) Western blot analysis of HER2 protein levels in breast cancer cell lines with varying HER2 gene copy number.

FIG. 17. Triplex formation induces double strand breaks. (FIG. 17A) Neutral single cell comet assay of untreated and HER2-205 treated cells. (FIG. 17B) Measurement of comet tail moment 24 h post-treatment of MCF7 (2 copies), MDA-MD-453 (11 copies) and BT-474 (52 copies).

FIG. 20. FIG. 20A: In vivo effect of HER2-205 on human breast xenografts. Human BT474 breast cancer xenografts were generated by subcutaneous injection into the flanks of female ovariectomized athymic nude mice. Treatment groups include: Vehicle (n=3) and HER2-205 (n=3). Twenty-eight days after implantation, the mice were treated by intraperitoneal injection with a single dose of either PBS (vehicle) or 20 mg/kg of HER2-205. FIG. 20B: Tumor growth measurements versus days following tumor implantation are shown. Arrow indicates administration of dose.

DETAILED DESCRIPTION

Figure 11:
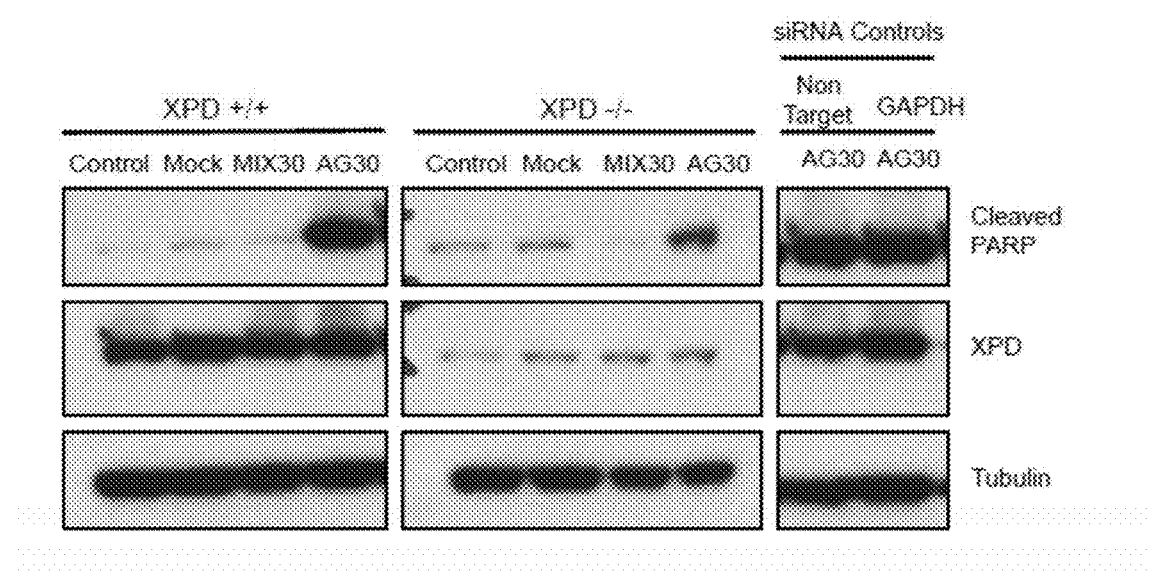
FIG. 11. Analysis revealed no reduction in the triplex-induced apoptosis levels in cells that had been treated with either non-target or GAPDH siRNA controls compared to XPD-proficient cells.

As described herein, triplex DNA formed at chromosomal sites by exogenous triplex-forming oligonucleotides (TFOs) induces apoptosis in human cells. Apoptosis is induced in response to formation of multiple triplex structures, not just one or two triplex structures, because the nucleotide excision repair (NER) pathway is capable of efficiently repairing a low level of damage.

DNA sequences capable of forming triplexes are prevalent in the human genome and have been found to be intrinsically mutagenic. Consequently, a balance between DNA repair and apoptosis is critical to counteract their effect on genomic integrity. The initial reaction of the cell to DNA damage is to repair the damage. However, if significant damage has been sustained and the DNA is irreparably compromised the cell switches to cell cycle arrest or to apoptosis. Perhaps the most versatile DNA damage removal system is the nucleotide excision repair (NER) pathway. This pathway is responsible for the removal of bulky, helix-distorting structures, including lesions produced by triplex formation. Triplex-forming oligonucleotides (TFOs) create a helical distortion upon binding to duplex DNA that strongly provokes NER-dependent DNA repair. When low-levels of triplex-distorting damage are produced, NER participates in damage repair. However, when excessive DNA damage is induced by the formation of multiple triplex structures, apoptosis prevails. Hence, triplex-induced DNA damage can be exploited to provide the foundation for a totally new therapeutic approach: tumor-specific induction of apoptosis in cancers characterized by gene amplification through the formation of multiple triplex structures at specific amplified gene sequences.

As described herein, triplex-forming oligonucleotides can be used to form altered helical distortions in a cell (e.g. a cancer cell) and pro-apoptotic pathways are activated by the formation of triplex structures. Moreover, the TFIIH factor, XPD, occupies a central role in triggering apoptosis in response to triplex-induced DNA strand breaks. Triplexes are capable of inducing XPD-independent double strand breaks, which result in the formation of γH2AX foci. Without wishing to be bound by any particular theory, it has been demonstrated that XPD is subsequently recruited to the triplex-induced double strand breaks and co-localized with γH2AX at the damage site. Furthermore, phosphorylation of H2AX at tyrosine residue 142 can stimulate the signaling pathway of XPD-dependent apoptosis. This mechanism may play an active role in minimizing genomic instability induced by naturally occurring non-canonical structures, perhaps protecting against cancer initiation.

Key proteins that contribute to cellular survival by acting in DNA repair can become executioners in the face of excess DNA damage. Studies suggest that some proteins required for efficient nucleotide excision repair (NER) may also play a role in apoptosis (1). The XPD protein has been identified as having two primary functions in NER: (i) stabilization of the transcription factor complex TFIIH and (ii) 5'→3' helicase function (2). In addition to its function in NER, transcription and possibly cell cycle regulation, XPD is also required for p53-mediated apoptosis (3-5).

The NER pathway occupies an important position in the recognition and repair of a wide array of helix distorting lesions. Previous studies have shown that high affinity DNA binding molecules can create helical distortions upon binding to duplex DNA that strongly provoke NER dependent repair (6,7). However, it was unknown whether formation of these structures caused a severe enough alteration in the DNA double helix to trigger activation of apoptotic pathways. Triplex DNA is formed when triplex-forming oligonucleotides (TFOs) bind as third strands in a sequence-specific manner within the major groove of duplex DNA at polypurine stretches. These molecules provide a means to experimentally create bulky helical distortions that are subject to NER and afford an opportunity to evaluate cellular responses to increasing levels of structurally induced DNA damage.

The human genome includes DNA sequence patterns that can adopt a variety of alternative structures in addition to the B-conformation described by Watson and Crick (8). For example, H-DNA (triplex) formation is favored by sequences that contain mirror repeat symmetry and occurs at purine/pyrimidine tracts (9-11). Naturally occurring sequences capable of forming H-DNA are found in the human genome as frequently as 1 in every 50,000 base pairs (12). Formation of these structures cause severe genomic alterations and represent an endogenous source of genotoxic stress (12,13). For instance, the H-DNA forming sequence located in the promoter region of the c-myc gene has been implicated in the translocation of the gene in Burkitt's lymphoma (14). Because the triplex region found in endogenous H-DNA is similar in structure to intermolecular triplexes formed by TFOs, they represent an excellent model to study the molecular pathways that determine cellular fate in response to endogenous sources of genotoxic stress.

As demonstrated herein, the formation of multiple (e.g. more than 2) triplex structures in a cell provokes apoptotic responses and reveals an XPD-dependent mechanism that modulates survival/apoptotic decisions in response to structurally induced DNA damage. In conjunction with the use of an established cell line and a transgenic mouse model containing multiple chromosomal target sites, sequence-specific TFOs were used to synthetically create altered helical structures. In some embodiments, at least 3, 4, 5, 6, 7, 8, 9, 10, 15, 20, 50 or more triplex structures are formed in the cell. The number of triplex structures formed by the TFM in a cancer cell characterized by gene amplification is greater than the number of triplex structures formed by the TFM in a normal cell (e.g., not a cancer cell).

As used herein, triplex-forming molecules (TFMs) such as triplex-forming oligonucleotides (TFOs), refer to oligonucleotides of any nucleic acid sequence that can bind to a polypurine site within an amplified cancer gene and form a triplex structure. The polypurine site within an amplified cancer gene is referred to a target site. One advantage of the methods and compositions described herein is that TFMs are "active" and bind their target sites, particularly target polypurine sites, and induce apoptosis in target cells (e.g. cancer cells or other abnormal cells which comprise at least one amplified gene) and not in healthy cells, thus avoiding adverse effects on healthy cells. In some embodiments, the TFO comprises the nucleic acid sequence provided by HER2-1 (SEQ ID NO: 15: 5'-GGGAGGAGGAGGTG-GAGGAGGAAGAGGA). In some embodiments, the TFO comprises the nucleic acid sequence provided by HER2-205 (SEQ ID NO: 16: 5'-GAGGAGGAGTGGGA-GAATGGGGGG).

As also described herein, triplex-induced double strand breaks (DSBs) stimulate cells to activate apoptosis both in vitro and in vivo. Although knockdown of XPD did not modulate the extent of triplex-induced DSBs, its depletion resulted in a decrease in triplex-induced apoptosis. Further investigation determined that XPD is recruited to the H2AX serine139 phosphorylation site and its presence is required for the phosphorylation of the H2AX tyrosine142 residue, which has been shown to be an essential post-translational modification for the recruitment of pro-apoptotic factors to the tail of γH2AX. These results identify a new role for XPD in addition to its previously reported requirement for p53-mediated apoptosis in regulating cellular fate decisions. Results support a key role for XPD-dependent apoptosis in preserving genomic integrity in the presence of excessive structurally induced DNA damage.

The methods and compositions provided herein relate to entry of TFMs into cells in order to bind the target site in sufficient quantity to induce apoptosis. TFMs, such as TFOs, can be introduced into a cell by any method known in the art, such as through modification of the oligonucleotide backbone or the use of a carrier or transport agent, which can be attached (covalently or non-covalently) to the TFM or mixed with (and not attached or conjugated to) TFMs. For example, hydrophobic molecules, such as lipids, (e.g., cationic lipids including transfection reagents), cell-penetrating peptides (CPP) and cell-targeting ligands can be used to enhance the ability of TFMs, such as TFOs, to enter cells/improve their interaction with the cell membrane lipid (hydrophobic) bi-layer. In some embodiments, the method of introducing TFMs, such as TFOs, into a cell involves electroporation.

In some embodiments, the TFMs are introduced into a cell using a population of nanoparticles. Nanoparticles compatible for use in the methods and compositions described herein will be apparent to one of skill in the art. In some embodiments, the nanoparticles are polymeric nanoparticles. In some embodiments, the TFMs, such as TFOs, are encapsulated within the nanoparticles. In some embodiments, the TFMs, such as TFOs, are linked or conjugated to the nanoparticles.

In specific embodiments, transport peptides (also known as protein transduction domains (PTDs), membrane translocating sequences (MTSs), and Trojan peptides) are used to enhance/facilitate uptake of TFOs into cells. Any cell-penetrating peptide capable of assisting or facilitating the entry of a TFM into a cell is compatible with the present disclosure. CPPs are short peptides (≤40 amino acids) that are cationic, able to enter many cell types, and typically made up of mostly hydrophilic amino acids/rich in arginine and lysine. They have been shown to be able to carry many types of entities, including oligonucleotides, into cells. Hydrophilic CPPs include, but are not limited to: Penetratin or Antenapedia (RQIKIWFQNRRMKWKK (SEQ ID NO: 1) or alternatively, PTD RQIKWFQNRRMKWKK (SEQ ID NO: 2)); HIV TAT protein (YGRKKRRQRRR (SEQ ID NO: 3)); SynB1 (RGGRLSYSRRRFSTSTGR (SEQ ID NO: 4)); SynB3 (RRLSYSRRRF (SEQ ID NO: 5)); PTD-4 (PIRRRKKLRRLK (SEQ ID NO: 6)); PTD-5 (RRQR-RTSKLMKR (SEQ ID NO: 7)); FHV Coat-(35-49) (RRRRNRTRRNRRRVR (SEQ ID NO: 8)); BMV Gag-(7-25) (KMTRAQRRAAARRNRWTAR (SEQ ID NO: 9)); HTLV-II Rex-(4-16) (TRRQRTRRARRNR (SEQ ID NO: 10)); D-Tat (GRKKRRQRRRPPQ (SEQ ID NO: 11)); and R9-Tat (GRRRRRRRRRPPQ (SEQ ID NO: 12)). Such CPPs can be covalently or non-covalently linked to TFMs, such as TFOs, or not linked to TFMs, such as TFOs; in the latter case, TFMs (TFOs) and CPPs are unconjugated when administered. In both embodiments, a sufficient quantity of TFMs (TFOs) and CPPs is administered to result in formation of multiple triplexes and induce apoptosis in the target cells. In the cells, TFMs, such as TFOs, bind their target sites. In some embodiments, the transport peptide is the Antennapedia peptide or fragment thereof. In some embodiments, the transport peptide is provided by the amino acid sequence of SEQ ID NO: 1. In some embodiments, the transport peptide is provided by the amino acid sequence of SEQ ID NO: 2.

In some embodiments, the transport peptide is the Antennapedia peptide comprises one or more modifications, such as the addition, deletion, or substitution of at least one amino acid. In some embodiments, the modification of the Antennapedia peptide is the presence of at least one additional terminal lysine residue.

One embodiment described herein is a method of inducing apoptosis in cancer cells comprising (that comprise)/are characterized by an amplified cancer gene, comprising contacting cancer cells comprising an amplified cancer gene with (a) triplex forming molecules (TFMs), such as triplex forming oligonucleotides (TFOs), specific for a (at least one, one or more) polypurine site (a, at least one, one or more) target site) in the amplified cancer gene and (b) a (at least one, one or more) transport peptide, under conditions under which TFMs (TFOs) and transport peptides enter cancer cells and TFMs (TFOs) enter the cancer cells in sufficient quantity, bind the polypurine site(s) and induce apoptosis. In some embodiments, the TFMs, such as TFOs, and transport peptides are linked, either covalently or non-covalently. Methods of covalently linking a TFM such as a TFO to a peptide such as a transport peptide will be known in the art. In some embodiments, the TFMs, such as TFOs, and transport peptides are not linked/are mixed or combined and are contacted with cancer cells as a mixture or combination. In some embodiments, the TFM and transport peptides are mixed or combined in the presence of a pharmaceutically acceptable carrier, excipient, or buffer compatible with administration to an individual.

In some embodiments, the amplified cancer gene is HER2 and the cancer cells are breast cancer cells or ovarian cancer cells. In some embodiments, the cancer cells are in an individual. In some embodiments, the individual is a human. In some embodiments, the individual is a woman.

In some embodiments, the cancer gene is a gene in the TABLE and cancer cells are of cancer type corresponding to the gene in the TABLE. In some embodiments, the cancer gene is HER2 and the cancer cells are breast cancer cells or ovarian cancer cells. In some embodiments, the cancer cells are in an individual. In some embodiments, the individual is a human.

In other aspects, methods of creating triplex-induced strand breaks, such as double strand breaks, in genomic DNA in cells (such as cells that comprise amplified DNA (genomic DNA), such as an amplified cancer gene) sufficient to induce apoptosis in the cells are provided. The method comprises introducing into the cells purine-rich (such as guanine-rich) triplex forming molecules, such as triplex forming oligonucleotides (TFOs) that bind a (at least one, one or more) polypurine site of genomic DNA in the cells in sufficient quantity to form multiple apoptosis-inducing triplexes in the genomic DNA.

In some embodiments, a (at least one, one or more) transport peptide is introduced into the cells with TFMs, such as TFOs; TFMs/TFOs, and transport peptides are (a) linked, either covalently or non-covalently or (b) not linked/are mixed or combined and are contacted with cancer cells as a mixture or combination. In some embodiments, the amplified cancer gene is HER2 and the cancer cells are breast cancer cells or ovarian cancer cells. In some embodiments, the cancer cells are in an individual. In some embodiments, the individual is a human. In some embodiments, the individual is a woman. In some embodiments, the cancer gene is a gene in the TABLE and cancer cells are of cancer type corresponding to the gene in the TABLE.

Other aspects relate to methods of inducing apoptosis of cancer cells characterized by an amplified cancer gene comprising contacting the cell with a TFM and a population of nanoparticles under conditions in which TFMs, such as TFOs, and the nanoparticles enter the cell and the TFM binds a target site in sufficient quantity to induce apoptosis.

In any of the embodiments, one or more different TFMs (e.g., 2, 3, 4, 5, 6, 7, 8, 9, 10 or more different TFMs), such as one or more different TFOs, can be used. For example, one type of TFM, such as one type of TFO, to a first/that binds a first polypurine site and a second, different TFM, such as a second, different TFO to/that binds a second, different polypurine site can be administered. The first and second polypurine sites (target sites) can be in the same amplified gene (e.g., both are in one amplified cancer gene, such as HER2) or in different amplified genes (e.g., one polypurine site is in a first amplified gene and the second polypurine site is in a second, different amplified gene). It is also possible that the same polypurine site (target site) is present in two different amplified cancer genes, in which case one type of TFM, such as one type of TFO, can be used. All transport peptides can be the same or a combination of several types of transport peptides can be used in the embodiments described.

The disclosure also provides compositions comprising a (at least one, one or more) triplex forming molecule (TFM), such as a triplex forming oligonucleotide (TFO) and a (at least one, one or more) transport peptide. In some embodiments, the compositions comprise a (at least one, one or more) triplex forming molecule (TFM), such as a triplex forming oligonucleotide (TFO) and a population of nanoparticles.

In some embodiments, the TFO binds a polypurine site (target site) of a (at least one, one or more) gene amplified in cancer cells and the transport peptide(s) is/are a (at least one, one or more) cell penetrating peptide(s). In some embodiments, the at least one, one or more transport peptide(s) is/are all or a fragment of Antennapedia peptide (the homeodomain of the *Drosophila* homeoprotein Antennapedia (residues 43-58) having all or a portion of sequence RQIKIWFQNRRMKWKK (SEQ ID NO: 1) (also represented Arg Gln Ile Lys IleTrp Phe Gln Asn Arg Arg Met Lys Trp LysLys), all or a portion of sequence PTD RQIKWFQNRRMKWKK (SEQ ID NO: 2) or a modification of the Antennapedia peptide of either sequence RQIKWFQNRRMKWKK (SEQ ID NO: 1) or PTD RQIKIWFQNRRMKWKK (SEQ ID NO: 2). In some embodiments, the modification of the Antennapedia peptide is the presence of at least one additional terminal lysine.

Aspects of the disclosure relate to methods of inducing apoptosis of cancer cells. In some embodiments, the cancer cells comprise or are characterized by an amplified cancer gene. As used herein, an amplified cancer gene refers to gene that has an increased copy number as compared to the copy number of the gene in a normal cell (not a cancer cell). The increase in copy of number of the amplified gene may result in overexpression of the gene. In cases in which the amplified gene is a cancer gene (e.g. an oncogene or a cancer associated gene), amplification and overexpression can result in cancer. In some embodiments, the amplified cancer gene is a gene presented in the TABLE. In some embodiments, the cancer type is presented in the TABLE. In some embodiments, the amplified cancer gene is a gene in the TABLE and the cancer cells are of the cancer type corresponding to the gene in the TABLE. In some embodiments, the amplified cancer gene is HER2. In some embodiments, the cancer type is breast cancer or ovarian cancer. In some embodiments, the amplified cancer gene is HER2 and the cancer type is breast cancer or ovarian cancer.

TABLE

Amplified and Overexpressed Genes in Human Cancer
(Source: T. Santarius et al., Medscape Today. A Census of Amplified and Overexpressed Genes in Human Cancer)

| Cancer type | Gene |
|---|---|
| Acute myeloid leukemia | TRIB1 |
| Bladder | YWHAQ, E2F3, YWHAZ, ERRB2, AURKA |
| Breast | SHC1, CKS1B, RUVBL1, C8orf4, LSM1, FGFR1, BAG4, MTDH, MYC, EMSY, PAK1, CDK4, MDM2, PLA2G10, STARD3, GRB7, RPS6KB1, PPM1D, CCNE1, |

TABLE-continued

Amplified and Overexpressed Genes in Human Cancer
(Source: T. Santarius et al., Medscape Today. A Census of
Amplified and Overexpressed Genes in Human Cancer)

| Cancer type | Gene |
| --- | --- |
| | YWHAB, ZNF217, AURKA, PTK6, CCND1, NCOA3, ERBB2 |
| Colorectal | MYC, EGFR |
| Diffuse large B cell lymphoma | REL |
| Endometrial | ERBB2 |
| Gastric | RAB23, MET, MYC, ERBB2, CDC6 |
| Glioma | MDM4, EGFR, CDK4, MDM2, AKT3, CCND2, CDK6, MET |
| Head and neck | DCUN1D1 |
| Hepatocellular carcinoma | CHD1L |
| Hodgkin's lymphoma | REL |
| Laryngeal squamous cell carcinoma | FADD |
| Liver | YAP1, BIRC2 |
| Lung | MYCN, EGFR, MET, WHSC1L1, YWHAZ, MYC, CCND1, MDM2, BCL2L2, PAX9, NKX2-1, KIAA0174, DCUN1D1, EEF1A2, MYCL1, SKP2, NKX2-8 |
| Malignant melanoma | MITF, CCND1, CDK4 |
| Medulloblastoma | MYC |
| Melanoma | C-MYC, C-RAS |
| Neuroblastoma | MDM2, MYCN |
| Oesophageal | PRKCI, ZNF639, SKP2, EGFR, SHH, DYRK2, ERBB2, CCNE1, AURK |
| Oral squamous cell carcinoma | CCND1 |
| Osteosarcoma | COPS3 |
| Ovarian | EIF5A2, EVI1, EMSY, ERBB2, RPS6KB1, AKT2, RAB25, PIK3CA |
| Pancreatic | ARPC1A, SMURF1, MED29 |
| Pancreatobillary | GATA6 |
| Prostate | MYC, AR |
| Retinoblastoma | E2F3, MDM4 |
| Rhabdomyosarcoma | MYCN, FGFR1, GPC5 |
| Sarcoma | JUN, MAP3K5, YEATS4, CDK4, DYRK2, MDM2 |
| Soft tissue sarcoma | SKP2 |
| Testicular germ cell tumour | KIT, KRAS |
| Wilm's tumour | CACNA1E |

Key: AR, androgen receptor; ARPC1A, actin-related protein complex ⅔ subunit A; AURKA, Aurora kinase A; BAG4, BCL-2 associated anthogene 4; BCL2L2, BCL-2 like 2; BIRC2, Baculovirus IAP repeat containing protein 2; CACNA1E, calcium channel voltage dependent alpha-1E subunit; CCNE1, cyclin E1; CDK4, cyclin dependent kinase 4; CHD1L, chromodomain helicase DNA binding domain 1-like; CKS1B, CDC28 protein kinase 1B; COPS3, COP9 subunit 3; DCUN1D1, DCN1 domain containing protein 1; DYRK2, dual pecificity tyrosine phosphorylation regulated kinase 2; EEF1A2, eukaryotic elongation transcription factor 1 alpha 2; EGFR, epidermal growth factor receptor; FADD, Fas-associated via death domain; FGFR1, fibroblast growth factor receptor 1, GATA6, GATA binding protein 6; GPC5, glypican 5; GRB7, growth factor receptor bound protein 7; MAP3K5, mitogen activated protein kinase kinase kinase 5; MED29, mediator complex subunit 5; MITF, microphthalmia associated transcription factor; MTDH, metadherin; NCOA3, nuclear receptor coactivator 3; NKX2-1, NK2 homeobox 1; PAK1, p21/CDC42/RAC1-activated kinase 1; PAX9, paired box gene 9; PIK3CA, phosphatidylinositol-3 kinase catalytic a; PLA2G10, phopholipase A2, group X; PPM1D, protein phosphatase magnesium-dependent 1D; PTK6, protein tyrosine kinase 6; PRKCI, protein kinase C iota; RPS6KB1, ribosomal protein S6 kinase 70kDa; SKP2, S-phase kinase associated protein; SMURF1, SMAD specific E3 ubiquitin protein ligase 1; SHH, sonic hedgehog homologue; STARD3, STAR- related lipid transfer domain containing protein 3; YWHAQ, tyrosine 3-monooxygenase/tryptophan 5-monooxygenase activation protein, zeta isoform; ZNF217, zinc finger protein 217.

EXAMPLES

Example 1

Materials and Methods

The following materials and methods were used in the work described herein.

Oligonucleotides. Oligonucleotides were synthesized with a 3'-amino-modifier C7 CPG (Glen Research) by the Midland Certified Reagent Company Inc. and purified by RP-HPLC. The sequence of the TFO, AG30, used and its target site are depicted in FIG. 1A. The G-rich TFO was also synthesized with the guanines in A8G30 replaced with 7-deaza-8-aza-guanine (PPG, G, Glen Research) as indicated in FIG. 1F. Third strand binding of the TFO to duplex DNA was measured by gel mobility assays as previously described (15). The control oligonucleotide, MIX30, a mixed base 30-mer, has the following sequence, 5'-AGTCA-GTCAGTCAGTCAGTCAGTCAGTCAG-3' (SEQ ID NO: 14). Labeled oligonucleotides were synthesized with 5'-rhodamine modifications using rhodamine phosphoramidite.

Cells Lines and Transfections. C127 cells were obtained from ATCC. The mouse epithelial cell line, AV16, containing ~100 randomly integrated chromosomal copies of the triplex target site were derived from the parental C127 cell line and target site copy number was determined using quantitative DNA dot blot analysis as previously described (16). A mouse fibroblast cell line with the λsupFG1 (lambda supFG1) vector chromosomally integrated and deficient in XPA was derived from transgenic mice carrying the λsupFG1 vector as a transgene and targeted disruptions in the NER gene, XPA. A similar cell line containing the λsupFG1 vector was derived from wild-type mice and used for comparison.

Cells were seeded in six-well plates at a density of $2 \times 10^5$ cells per well the day before transfection. Cells were transfected with 2 μg of AG3O or MIX30 using Oligofectamine (Invitrogen) transfection reagent. Transfection was performed as per manufacturer's instructions. siRNA directed against XPD, GAPDH and non-target controls (ON-Target plus SMARTpool reagents; Dharmacon) were transfected into AV16 cells using Dharmafect-1 transfection reagent (Dharmacon) according to the manufacturer's instructions. Western blot analysis was used to confirm knockdown of protein.

AV16 cells were used to generate XPD−/− cells using shRNA. Briefly, lentivirus shRNA vectors for XPD knockdown, were obtained from Sigma-Aldrich (XPD-18: TRCN0000071118; XPD-19: TRCN0000071119; XPD-58: TRCN0000338058). AV16 cells were transduced with Lentiviral expression constructs either for non-target shRNA or GFP shRNA or one of the three different shRNA targeting XPD (ERCC2). Stable clones expressing the shRNA were established via puromycin dihydrochloride selection (2 μg/ml). AV16 clone XPD-19-1 stably expressing shRNA XPD-19 was used in the mutagenesis experiments.

Metaphase Chromosome Spreads. AV16 cells were transfected with 2 μg of rhodamine labeled MIX30 or AG30. Twenty-four hours post-transfection, cells were treated for 5 h with Colcemid (0.1 μg/μl). Cells were then collected and washed once with PBS. To the cell pellet a 75 mM KCl solution was added for 20 minutes at 37° C. Cell pellets were then resuspended in Carnoy's fixative solution (75% methanol, 25% acetic acid). After 10 min incubation at room temperature, the cells were pelleted and resuspended in an additional 500 μl of Carnoy's fixative solution. Cells were dropped from a height onto glass slides and mounting medium with DAPI (Prolong Gold antifade reagent, Invitrogen) was added to each slide. Pictures were taken of 50-60 metaphase spreads using an Axiovert 200 microscope (Carl Zeiss Micro Imaging, Inc.).

Survival Assays. Cell survival was assayed either by visualization of monolayer growth or by colony formation. To quantify survival by monolayer growth, cells were seeded at a defined density in either 6 or 12 well dishes and treated with the TFO as previously described. Cells were stained with crystal violet 24, 48 and 72 hours post treatment for monolayer visualization. To assay for cell survival by clonogenic survival, cells were treated with 2 μg of AG30 or MIX30 for 48 h and then seeded at 250-500 cells per well. Colonies were washed with 0.9% saline solution and stained with crystal violet 10-14 days later. Colonies consisting of >50 cells were counted. Colony formation was normalized to plating efficiency of the non-treated cells. Errors bars in the survival analysis are based on three independent experiments.

Apoptosis Analysis. Cells were analyzed by flow cytometry 24 hrs post-treatment using the Annexin V-FITC/PI apoptosis detection kit (BD Pharmingen) according to the manufacturer's protocol. The apoptotic rate was calculated as the combined percentage of early apoptotic and late apoptotic cells. Data analysis was performed using FlowJo software.

Western Analysis. Floating and adherent cells were collected, cell pellets were lysed with RIPA buffer (150 mM NaCl, 0.1% SDS, and inhibitors), and 30-50 μg of total protein per sample was resolved by SDS-PAGE. Proteins were detected by a standard immunoblot protocol using the following primary antibodies: cleaved PARP; cleaved caspase-3; phospho-p53 (ser15); phospho-H2AX (serine 139); (Cell Signaling Technology, Inc. Danvers, Mass.); phospho-H2AX (tyrosine 142) (Millipore Corporation, Billerica, Mass.); XPD (BD Biosciences, San Jose, Calif.); tubulin (clone B-512; Sigma, St. Louis, Mo.). Each experiment was carried out a minimum of three times, and representative Western blots are shown.

Immunofluorescence. Cells, seeded onto UV-irradiated coverslips, were treated for 24 hrs and samples were prepared under reduced light as previously described (17). Cells were incubated with the following antibodies: rabbit anti-γH2AX antibody (Cell Signaling) and FITC-conjugated F(ab')2 fragment donkey anti-rabbit IgG (H+L) (Molecular Probes Inc.), and then stained with 100 ng/mL DAPI (Sigma). Images were captured using an Axiovert 200 microscope (Carl Zeiss Micro Imaging, Inc.).

Neutral Comet Assay. Cells were collected 24 h post-treatment and neutral comet assays were performed according to the manufacturer's protocol (Trevigen Inc) with one adjustment of $3.5 \times 10^5$ cells/ml for each single cell suspension. Comets were visualized using an Axiovert 200 microscope and analyzed with Comet Score™ software (TriTek Corp). Approximately 100-150 randomly selected, non-overlapping cells were analyzed per experiment. Results were expressed as mean tail moment.

In Vivo Analysis of Triplex-Induced DNA Strand Breaks. AV mice were derived from the CD1 background (Charles River Laboratories, Wilmington, Mass.) and were generated as previously described (18). DNA dot blot analysis confirmed the AV founder mouse to carry ~50 copies of the triplex target site in its genome. AV mice or CD1 control mice (14-days old) were treated by i.p. injection with PBS, MIX30, or AG30 (50 mg/kg). Three mice were used per treatment group. Mice were sacrificed 6 hours after treatment and tissue samples were collected. Spleen tissue was collected and fixed in 4% paraformaldehyde overnight at 4° C., embedded in paraffin and cut into sections for evaluation by immunohistochemistry. Cut sections were stained for phospho-H2AX (Cell Signaling) and activated caspase 3 (Abcam) and analyzed by microscopy. All sections were analyzed and quantified by counting 12 randomly selected sections of the same sample. The number of cells positive for activated caspase 3 and γH2AX were manually counted on digital images of the specimens. The differences in the percentage of positive cells were analyzed by one way Anova and tukey test as posthoc. Representative depiction of immunohistochemistry is shown. Animal studies were approved and performed according to the guidelines of the Institutional Animal Care and Use Committee of Yale University.

Coimmunopreciptation. AV16 cells were transfected with AG30 or MIX30 and 24 hrs post-transfection, cells were lysed in IP lysis buffer (Thermo Scientific). To observe the interaction of XPD with γH2AX, cell lysates were immunoprecipitated with polyclonal rabbit antibody γH2AX (Santa Cruz) or rabbit IgG (Jackson Immunoresearch Lab) using protein A/G beads (Santa Cruz) at 4° C. for 90 minutes. The immunoprecipitated complex was analyzed by immuno-blotting.

Cell Cycle Analysis and γH2AX. AV16 cells were collected at 6 and 24 hrs following transfection with either MIX30 or AG30. After washing once with PBS, the cells were fixed in 1% paraformaldehyde for 15 min on ice. Cells were centrifuged and fixed in 70% ethanol at −20° C. for 2 hrs. The cells were then washed with BSA-T-PBS (1% w/v Bovine Serum Albumin and 0.2% v/v Triton X-100 in PBS) and incubated with γH2AX antibody (Cell Signaling) in BSA-T-PBS overnight at 4° C. After washing, the cells were incubated with anti-rabbit IgG Fab2 Alexa 488 (Molecular Probes) at room temperature for 1 h in the dark. Cells were washed and the pellet resuspended and incubated at room temperature in PI staining solution (PI/RNase solution, BD) for 15 minutes. Cells were analyzed by flow cytometry.

Mutagenesis Assay. The mouse cell lines were established with multiple chromosomally integrated copies of the recoverable λ supFG1 shuttle vector carrying the supFG1 reporter gene. Following 48-72 hrs of TFO treatment, genomic DNA was isolated and incubated with λ in vitro packaging extracts for shuttle vector rescue and reporter gene analysis as previously described (16,19). Briefly, functional supFG1 genes suppress the nonsense mutations in the host bacteria β-galactosidase gene yielding blue plaques in the presence of IPTG and X-Gal. If however a mutation occurs in the supFG1 gene, the amber mutation will not be suppressed and the resulting plaque will be white. Mutation frequency was calculated by dividing the number of colorless mutant plaques by the total number of plaques counted. Experiments were done in triplicate and standard errors were calculated for the mutation frequencies as indicated by the error bars.

Statistical Analysis. Differences in the mean number of γH2AX foci/cell, the number of apoptotic cells, and tail moment were analyzed by one way Anova and tukey test as posthoc. All statistical analyses were performed using Graphpad Prism software. *$p<0.001$, $p<0.01$, *$p<0.05$ Example 2

Triplex-Induced Apoptosis

Triplex Induced Cell Death

Using an assay to measure the induction of repair synthesis, research has determined that TFOs create a helical distortion upon binding to duplex DNA that strongly provokes DNA repair (6,7). Additional studies have confirmed the importance of the NER pathway in the recognition and repair of TFO-induced DNA alterations (7,20). In order to investigate the potential for helical distortions to induce apoptosis in cells, we generated a mouse epithelial cell line (AV16) with ~100 copies of randomly integrated chromosomal triplex target sites (FIG. 1A) (16). Triplex structures were synthetically generated using the TFO, AG30, which is designed to specifically bind to the polypurine target site (FIG. 1A). Through the use of a restriction protection assay, AG30-induced triplex formation has been previously detected at a chromosomally integrated target site (21). To confirm chromosomal binding of AG30 in our cell line, we prepared non-denatured metaphase chromosome spreads from AV16 cells that had been treated. Johnson et al. have previously described a method for detecting third-strand binding to non-denatured fixed metaphase spreads (22). In order to detect triplex formation in vivo, we modified their technique by treating the cells prior to generation of the metaphase chromosome spreads. AV16 cells were treated with either 2 μg of rhodamine labeled AG30 or the control mixed sequence oligonucleotide MIX30, which cannot bind as a third strand to the target polypurine/polypyrimidine sites in the AV16 cells. Twenty-four hours post-treatment, cells were treated for 5 hrs with Colcemid and then collected and prepared as non-denatured fixed metaphase chromosome spreads according to the protocol previously described (22). In order to minimize background fluorescence created by the presence of unbound oligonucleotides and non-specific binding events, multiple washes were incorporated during the preparation of the metaphase spreads. It has been previously established that the DNA of non-denatured fixed metaphase spreads remains in a duplex state (22). Thus, the generation of chromosomal AG30-foci under the conditions of this assay represents third strand binding to fixed chromosomes with intact DNA double helix. As shown in FIG. 1B, several rhodamine-AG30 chromosomal foci were detected 24 h post-transfection in the AV16 cell-derived metaphase spreads, in contrast to the rhodamine-MIX30 treated cells. These results provide evidence for third strand binding by AG30 to multiple chromosomal sites, with 45% of AV16 cells treated with rhodamine-AG30 being positive for chromosomal foci per cell (FIG. 1C) compared to ~10% of cells treated with MIX30. The binding of non-triplex forming oligonucleotides like MIX30 to DNA requires single stranded targets. As a result, one would not expect to see high levels of non-specific chromosomal interactions with the MIX30 control. This is consistent with the fact that this mixed sequence oligonucleotide cannot form Hoogsteen or reverse Hoogsteen triplexes, even at high concentrations in vitro. Although there may be some non-specific retention of MIX30 leading to low levels of foci formation, this is just background to the assay. Treatment of the parental cell line (C127), which lacks the polypurine/polypyrimidine target site, with rhodamine-AG30 further confirms the specificity of third strand binding (FIG. 9A and FIG. 9B). Analysis of C127 cell-derived metaphase spreads revealed that ~13% of cells were positive for chromosomal foci per cell following treatment with either MIX30 or AG30. These results are supportive of our conclusions because both MIX30 and AG30 treatment of C127 cells resulted in the same non-specific background levels. The specific foci formation by AG30 in this assay provides evidence for third strand binding and triplex formation in the treated AV16 cells. The generation of rhodamine-AG30 foci likely represents several third strand binding events in proximity, and so these results support the formation of multiple triplex structures following AG30 treatment of AV16 cells. To this end, the results from these studies provide evidence that AG30-foci formation represents sequence-specific binding to its polypurine target site.

Following this validation, we proceeded to examine whether triplex formation was capable of inducing death in cells with multiple TFO target sites. The parental cell line, C127, which lacks the target site, served as a control to assess the possibility of non-specific oligonucleotide interactions that could result in cell death. Forty-eight hours after treatment, monolayer growth assays demonstrated a decrease in cell growth that correlated with the formation of triplex structures, suggesting that DNA helical distortions can lead to cell death (FIG. 1D). It is important to note that a decrease in cell growth following TFO treatment was only observed in AV16 cells, which have the potential to acquire multiple triplex structures and not in C127 cells, which lack the triplex binding site. In addition, growth inhibition was not observed in cells that were treated with the control oligonucleotide, MIX30. To further attribute a decrease in cell survival resulting from triplex formation, clonogenic survival studies were performed using AV16 cells. Only cells treated with AG30 experienced a decrease in cell survival (FIG. 1E). As observed in the monolayer assay, non-specific toxicity was not detected with either the transfection agent (mock treatment) or MIX30. The results obtained from the survival assays establish that helical distortions induced by the formation of triplex structures are capable of inducing cell death.

In order to investigate the possibility that the observed cell death could be attributed to G-quadruplex formation (23-25), A8G30 was designed with the same sequence as AG30 but with every third guanine substituted with the modified guanine base, 7-deaza-8-aza-guanine (PPG or G) (FIG. 1F). Studies have determined that substitution of every third guanine with PPG was sufficient to reduce self-association of TFOs containing long runs of guanines (26). To determine the relative binding affinities of the G-rich TFOs for the target duplex, a gel mobility shift assay was performed (FIG. 1G). The $K_d$ for each TFO was estimated as the concentration of TFO at which binding was one-half maximal. As shown in FIG. 1G, using buffer conditions that promote triplex formation, both TFOs bound to the target site with high affinity ($K_d$~1×10$^{-9}$ M). Treatment of AV16 cells with either AG30 or the PPG-substituted TFO, A8G30 resulted in a reduction in cell growth as observed by monolayer growth assay (FIG. 1H). Taken together, the inability of the control oligonucleotide to induce cell death and the induction of cell death after treatment with A8G30, show that the increase in cell death observed in the survival assays is a result of a specific and site-directed effect of AG30 binding to the chromosomal target site.

Triplex Induced Apoptosis

Studies were then initiated to determine whether the increase in cell death observed in the survival assays following TFO treatment resulted from the activation of a pro-apoptotic pathway. AV16 cells were treated with a mock transfection, MIX30, or AG30 and analyzed for induction of apoptosis 24 hrs post treatment by detection of Annexin-V binding using flow cytometry. Annexin-V binding to exposed phosphatidylserine residues in the cell membrane is an early marker of apoptosis and 23% of the AG30-treated cells were determined to be Annexin-V positive as a result of triplex induced helical distortions (FIG. 2A). Western blot analysis of caspase-mediated cleavage of Poly(ADP-ribose) polymerase (PARP) was also used to confirm triplex-induced apoptosis. PARP, a nuclear DNA binding protein that recognizes DNA strand breaks, is a substrate for caspase-3, and its cleavage is an early event in apoptotic response (27). Caspase-mediated cleavage of PARP was only detected in cell lysates isolated from AG30-treated AV16 cells (FIG. 2B). To confirm that the observed apoptosis resulted from triplex formation and not generation of G-quadruplexes, production of cleaved PARP was analyzed by Western blot analysis 24 hrs after transfection with either AG30 or A8G30. Similar levels of cleaved PARP were detected in cell lysates isolated from A8G30-treated AV16 cells compared to AG30-treatment, suggesting that the observed apoptosis can be primarily attributed to triplex formation (FIG. 2C). Triplex-induced apoptosis was detected as early as 6 hrs and up to 72 hrs post TFO-treatment as determined by Western blot analysis (FIG. 2D).

To test the impact of multiple triplex structure formation on the level of induced apoptosis, AV16 cells were exposed to increasing concentrations of AG30. As shown in FIG. 2E, the percentage of Annexin-V positive cells increased with higher concentrations of TFO treatment. Treatment with a low concentration of AG30 (50 nM) resulted in an Annexin-V positive population of ~8%, which was slightly higher than that of background (~6%). The percentage of Annexin-V positive cells plateaued at ~60% following treatment with 200 nM of AG30. Moreover, no increase in the level of apoptotic cells was observed in the cells treated with increasing concentrations of the control oligonucleotide, further confirming that the observed apoptosis can be attributed to the formation of altered helical structures and not due to non-specific toxicity generated by the oligonucleotide itself. As shown in FIG. 2F, clonogenic survival studies correlate with these results, with the surviving cell fraction decreasing with increasing AG30 concentration. Collectively, these results support a mechanism that alterations to the DNA duplex structure created by the formation of multiple triplex structures is capable of inducing apoptosis.

Triplex-Induced DSBs

To determine whether TFO-induced altered helical structures can act as a fragile site resulting in DSBs, we performed neutral comet assays. Single cell "comets" were observed microscopically after separation of DNA fragments from the cells by electrophoresis (FIG. 3A). Using the "comet tail moment" as a measure of the extent of DNA breakage, we assessed the presence of DSBs resulting from triplex formation. As shown in FIG. 3A, we determined that AG30 treatment resulted in more DSBs compared to untreated and MIX30-treated cells.

Histone variant H2AX becomes phosphorylated on serine139 (γH2AX) in response to DNA damage that involves formation of DSBs (28) and foci formation is frequently used as a quantitative marker for DSBs in immunofluorescence microscopy (29). The presence of triplex-induced DSBs was also determined by co-staining for γH2AX and DAPI 24 hrs after treatment (FIG. 3B). AV16 cells treated with AG30 resulted in the formation of more γH2AX nuclear foci compared with untreated cells (FIG. 3C). Western blot analysis of γH2AX also confirms the presence of H2AX S139 phosphorylation in only the AG30-treated cells, in agreement with the immunofluorescence results (FIG. 3D). These data suggest that the formation of triplex structures in cells that contain multiple target sites generates substantial DSBs, which may overwhelm the cell's repair capacity causing the initiation of an apoptotic response.

To ensure that the presence of γH2AX foci was truly a hallmark of DSBs and not generated in the course of DNA fragmentation during apoptosis, we utilized a multiparameter cytometry assay (30-32). The presence of triplex-induced DSBs was determined using flow cytometry by staining for γH2AX in the presence of propidium iodine. γH2AX expression attributed to DSBs is cell cycle independent, while high intense γH2AX expression in S-phase is associated with apoptosis (30). Cells were harvested 6 hrs and 24 hrs after treatment with AG30. Flow cytometry analysis of γH2AX expression during the cell cycle indicated increased levels of γH2AX in all phases of the cell cycle of AV16 cells 6 hrs after exposure to AG30 (FIG. 3E). This signal persisted for up to 24 hrs after TFO-treatment and increased to 21.7% (FIG. 3E), suggesting that many sites marked by γH2AX foci remained unrepaired. Analysis of the FACS profiles indicates that γH2AX expression in AG30-treated cells was significantly higher compared with mock treated and MIX30-treated cells (FIG. 3F).

In Vivo Generation of Triplex-Induced DSBs

To evaluate the potential for triplex DNA to induce DSBs in vivo, we utilized a transgenic mouse model (AV mouse), with ~50 copies of the triplex target sequence chromosomally integrated into its genome (FIG. 4A) (18). Immunohistochemistry staining for γH2AX and the apoptosis marker, activated caspase 3 was used to assess the cellular response to in vivo triplex formation. AV mice were administered a 50 mg/kg dose of MIX30 or AG30 via intraperitoneal injection (i.p.). In order to investigate the extent of triplex-induced DNA strand breaks, we performed immunohistochemistry staining of γH2AX as a marker for ongoing DNA damage on spleen tissue harvested 6 h post-treatment. Low levels of γH2AX staining were observed in the spleens of mice that had received i.p. doses of the control oligonucleotide, MIX30 (FIG. 4B,C). In contrast, AG30 treatment triggered an increase in the percentage of cells positive for γH2AX foci compared to the PBS and MIX30 treated mice (FIG. 4B,C). To further substantiate the specificity of triplex induced γH2AX foci, CD1 control mice, which lack the triplex target site, were also administered a 50 mg/kg dose of AG30. Immunohistochemistry analysis of spleen tissue revealed no increase in the percentage of cells positive of γH2AX foci above background (FIG. 10A-10C). An increase in the production of γH2AX foci solely in the AV mice after AG30 treatment indicate the presence of triplex-induced DSBs. Immunohistochemistry staining for activated caspase 3 was then used to determine if the formation of triplex-induced γH2AX foci could elicit an apoptotic response in vivo. Mice treated with the control oligonucleotide, MIX30 showed almost a complete absence of activated caspase 3 staining in their spleens 6 h following treatment (FIG. 4B,D). However, analysis of spleens from AV mice dosed with AG30 revealed that 26% of their spleen cells were positive for activated caspase 3 staining (FIG. 4B,D). Examination of spleen tissue samples obtained from CD1 mice treated with AG30 determined a non-existence of activated caspase 3 6 h post-treatment (FIGS. 10A-10C). Altogether, these results are consistent with the interpretation that the formation of endogenous triplex structures can result in DSBs, which can in turn prompt the activation of apoptosis.

NER Deficiency Results in Increased Apoptosis Levels

Activation of apoptosis in response to DNA damage provides a default mechanism that can be implemented to prevent clonal expansion of cells with unrepaired damage. As a result, studies were initiated to investigate cellular response to triplex-induced DSBs under circumstances where cells may be ineffective at repair. XPA is a key NER factor responsible for verifying altered DNA conformations, and is crucial for correct assembly of the remaining repair machinery around a lesion (33). Previous studies have determined that TFOs were capable of binding to duplex DNA and creating altered helical structures that strongly provoked XPA-dependent DNA repair. To investigate whether triplex formation induced DSBs in an XPA-dependent manner, we treated XPA-proficient and XPA-deficient mouse fibroblast cells with a mock transfection, MIX30 or AG30. Cells were harvested 24 hrs following treatment and through the use of flow cytometry, we evaluated the levels of triplex-induced DNA strand breaks by staining for γH2AX. Analysis of γH2AX expression levels as a measure of double strand break formation indicated increased levels of γH2AX in both the XPA-proficient and—deficient cells following AG30-treatment (FIG. 5A). Exposure to AG30 increased γH2AX expression in XPA-proficient cells to 22%, and a similar expression level of 28% was observed in the XPA-deficient cells (FIG. 5A).

We then proceeded to evaluate induced apoptosis levels as a result of triplex-induced DNA strand breaks in XPA-deficient cells. XPA-deficient cells were treated with a mock transfection, MIX30, or AG30 and analyzed for the induction of apoptosis. Following 24 hr administration of AG30, 55% of the deficient cells were determined to be Annexin V positive compared to 32% of the AG30-treated NER-proficient cells (FIG. 5B). Western blot analysis of cleaved PARP also indicated an increase in apoptotic cell death in the absence of XPA (FIG. 5C). These findings suggest that XPA is not required for activation of apoptosis, despite its importance in the repair of triplex structures. Furthermore, these results support the conclusion that a loss of XPA, and possibly functional NER, leads to an increase in apoptosis in response to triplex-induced double strand breaks.

XPD Requirement for Triplex-Induced Apoptosis

After determining that activation of apoptosis was a cellular response to extensive triplex-induced DNA strand breaks both in vitro and in vivo, we were interested in determining which proteins were involved in maintaining the switch from DNA repair to apoptosis. We hypothesized that a dual role NER protein like XPD, which contributes to genomic stability by participating in both repair and apoptosis, may also aid in triggering the cell to activate a pro-apoptotic pathway in the presence of excessive triplex-induced DNA double strand breaks. AV16 cells proficient or deficient for XPD were treated with AG30 and analyzed for the activation of apoptosis. As expected, monolayer growth assays demonstrated a decrease in cell survival in the XPD-proficient cells (FIG. 6A). However, a decrease in cell growth was not observed following TFO treatment of the siRNA XPD-depleted cells, where the level of cell growth was similar to that of control cells. To further attribute a role for XPD in activating apoptosis in response to excessive DNA strand breaks induced by triplex structures, we also evaluated the level of Annexin-V positive cells. AG30 treatment of siRNA XPD-depleted cells resulted in a significant decrease in apoptosis ($p<0.001$) (FIG. 6B). Western blot analysis of cleaved PARP also supports a reduction in triplex-induced apoptosis that is contingent on XPD (FIG. 6C). To establish that the change in apoptosis did not result from siRNA off-target effects, we also evaluated cleaved PARP levels following AG30-treatment in AV16 cells that had been transfected with control siRNAs. This analysis revealed no reduction in the triplex-induced apoptosis levels in cells that had been treated with either non-target or GAPDH siRNA controls compared to XPD-proficient cells (FIG. 11).

XPD helicase mediates strand separation at the site of the DNA lesion (34). In addition, tumor suppressor p53, a central component of apoptosis, can bind to and inhibit its helicase activity. After AG30 treatment, we determined by Western blot that an increase in p53 protein levels corresponded to increased caspase-3 mediated cleavage of PARP in XPD-proficient cells (FIG. 6D). On the contrary, the relative amount of p53 protein remained stable following TFO treatment of XPD-depleted cells compared to untreated cells. Upon DNA damage, phosphorylation of p53 at serine 15 coordinates polyphosphorylation, maintains nuclear retention, and stabilizes the protein through disruption of MDM2 binding (35-37). As determined by Western blot analysis, triplex-induced DNA strand breaks resulted in increased phosphorylation of serine15 in XPD-proficient cells. However, a reduction in p53 phosphorylation at serine 15 was observed in the XPD-depleted cells (FIG. 6E).

To investigate whether the differential induction of apoptosis in XPD-proficient and deficient cells was the hallmark of a differential induction of DNA damage, we performed neutral comet assays. As shown, in FIG. 6F, triplex formation induced the same degree of DSBs in XPD-proficient cells as it did in the XPD-depleted cells verifying that triplex-induced DNA strand breaks is not dependent upon functional XPD. The results from these studies support a mechanism where XPD is important for activation of apoptosis and not required for the formation of triplex-induced DSBs.

Recruitment of XPD to the DSB Site

Figure 12A:
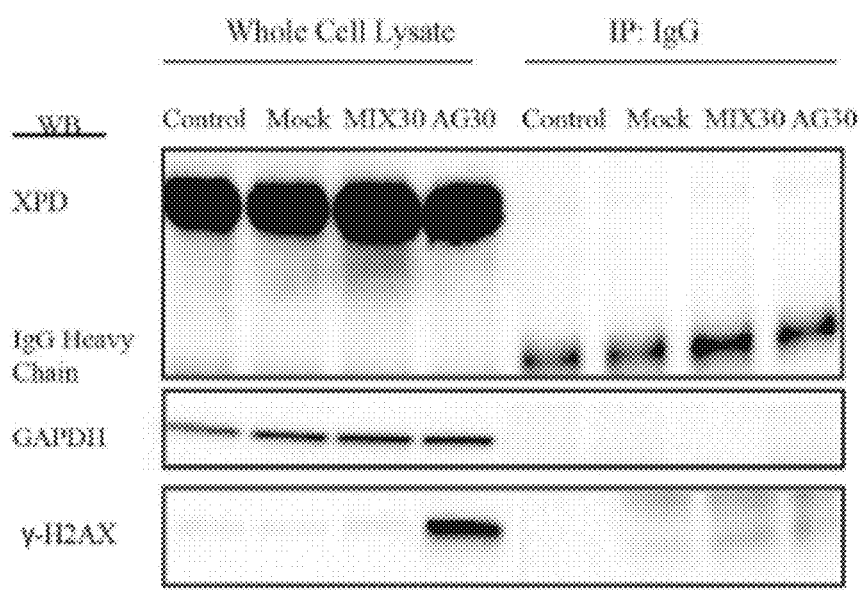
(FIG. 12A) Western blot analysis of the γH2AX-immunoprecipitation product revealed a signal for XPD in the AG30-treated AV16 cells that was substantially more robust than MIX30-treatment (FIG. 7C). These findings suggest that XPD is recruited to the site of damage and further supports the confocal microscopy results (FIG. 7C). As shown, the specificity of this interaction was confirmed with the absence of XPD and γH2AX in IgG co-immunno-precipitations).

XPD has been implicated in our studies to occupy an important role in activating apoptosis in response to triplex-induced DSBs. To determine whether XPD protein interacts with γH2AX foci, we treated AV16 cells with MIX30 or AG30. Confocal microscopy analysis indicates co-localization of XPD with γH2AX foci following treatment with the TFO, AG30 (FIG. 7A). Calculation of a co-localization coefficient using ImageJ demonstrates that XPD is mobilized to the triplex-induced DSB site (FIG. 7B). To further confirm XPD interactions with γH2AX foci, we treated AV16 cells with a mock transfection, MIX30 or AG30. Twenty-four hours after treatment, γH2AX was immunoprecipitated from cell lysates using protein A/G beads and probed for XPD by Western blot analysis. In whole cell lysates, γH2AX was detected by Western blot analysis only in the AG30-treated cells and similar levels of XPD were observed in all of the treatment groups. However, Western blot analysis of the γH2AX-immunoprecipitation product revealed a signal for XPD in the AG30-treated AV16 cells that was substantially more robust than MIX30-treatment (FIG. 7C). These findings suggest that XPD is recruited to the site of damage and further supports the confocal microscopy results (FIG. 7C). The specificity of this interaction was confirmed with the absence of XPD and γH2AX in IgG co-immunnoprecipitations (FIG. 12A).

In order to verify that XPD-depletion did not inhibit the formation of γH2AX foci, thus resulting in a reduction in triplex-induced apoptosis, we evaluated γH2AX foci formation in XPD-proficient and deficient cells following TFO treatment using immunofluorescene (FIG. 7D). A similar mean number of γH2AX foci/cell was observed following AG30 treatment in the XPD-depleted cells compared to the proficient cells (FIG. 7E). This implies that although XPD co-localizes at the DSB site, it is not required for γH2AX foci formation and supports our earlier data that shows that XPD is not required for triplex-induced double strand breaks.

Activation of Apoptosis Preserves Genomic Integrity

Apoptosis plays an important role in maintaining genomic integrity by providing a mechanism by which a cell can actively control its own death in response to a variety of DNA-damaging stimuli. Xia et al. (38) and Cook et al. (39) have independently discovered that the phosphorylation status of the tyrosine 142 residue (Y142) of H2AX is critical in determining the relative recruitment of either DNA repair or pro-apoptotic factors to the site of DSBs. Both groups demonstrate that unlike S139, Y142 is phosphorylated in normal undamaged cells. When repair is possible following DNA damage, Y142 is gradually dephosphorylated, allowing the γH2AX (S139 phosphorylation) modification and the recruitment of repair factors to occur. However, in cases where DNA damage is excessive Y142-phosphorylated H2AX persists in the presence of S139 phosphorylation. This doubly phosphorylated H2AX recruits pro-apoptotic factors like the JNK complex, an established inducer of apoptosis.

To establish a role for Y142 phosphorylation in regulation of the apoptotic response following triplex-induced DNA strand breaks, we probed both H2AX phosphorylation sites by Western blot analysis. NER-proficient and XPA-deficient cells were treated with AG30 and 24 hrs post-treatment cell lysates were prepared. As we observed in our previous experiments (FIG. 5C), triplex-induced DNA strand breaks resulted in the activation of apoptosis in both cell lines as determined by the presence of cleaved PARP (FIG. 8A). Although apoptosis was observed in both XPA-proficient and XPA-deficient cells following TFO-treatment, slightly higher levels of S139 phosphorylation was observed in the XPA-deficient cells suggesting the presence of more DSBs. In the case of the XPA-deficient cells an increase in the level of Y142-phosphorylation is also observed, compared to the XPA-proficient cells (FIG. 8A). Tyrosine 142-phosphorylation is a prerequisite for recruitment of the proteins necessary for apoptosis. These results correspond with our observation that there is a ~2-fold increase in apoptotic cells in XPA-deficient cells compared to XPA-proficient following AG30-treatment.

XPD-proficient and siRNA XPD-depleted cells were also treated with AG30 and 24 hrs post-treatment cell lysates were prepared. As we observed in our previous experiments, when AV16 cells were XPD-depleted using siRNA there was a decrease in the level of apoptotic cells (FIG. 8B). However, western blot analysis determined that the relative S139 phosphorylation level remained constant when XPD was depleted from the cells, although the induction of apoptosis was reduced (FIG. 8C,D). This supports our hypothesis that the reduction in apoptosis levels observed in XPD-deficient cells cannot be attributed to a decrease in triplex-induced DNA strand breaks and strongly supports that XPD is not required for triplex-induced DSBs. On the other hand, when the relative levels of Y142 phosphorylation were analyzed following TFO treatment there was a reduction in phosphorylation in the XPD-deficient cells, although the level of DNA double strand breaks was similar to that of the proficient cells (FIG. 8C,E). These results correspond with our observation that there is a decrease in apoptotic cells in XPD-deficient cells compared to XPD-proficient following AG30-treatment. These data support a model in which H2AX phosphorylation at residues S139 and Y142 is required for activation of apoptosis in response to triplex-induced DSBs (FIG. 8F). This would suggest that an absence of XPD disrupts the signaling pathway utilized to trigger apoptosis in the presence of DNA strand breaks induced by the formation of multiple triplex structures.

Following confirmation that apoptosis plays a key role in processing triplex-induced DNA DSBs, we proceeded to investigate its importance in preserving genomic integrity. Site-directed mutagenesis induced by triplex structures has been established in vitro and in vivo (40,41). Because cells defective in apoptosis tend to survive with excess damage, we examined the effect of XPD-depletion on triplex-induced genomic instability. Using an assay for targeted mutagenesis in mammalian cells, we evaluated triplex-induced mutations using AV16 cells, which contain ~100 copies of the λsupFG1 shuttle vector DNA in a chromosomal locus. Through the use of packaging extracts, the vector DNA can be isolated from genomic DNA into phage particles and subsequently analyzed for induced mutations. SupFG1 not only encodes an amber suppressor tRNA whose function can be scored in indicator bacteria, but also contains the AG30 triplex-binding site (16).

Figure 12B:
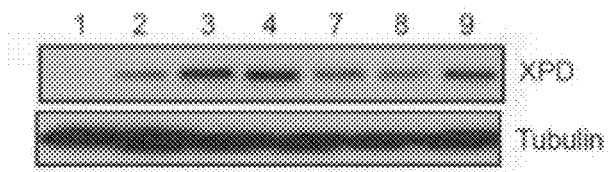
(FIG. 12B) AV16 and AV16 XPD-19-1 cells, which stably expressed XPD shRNA were treated with a mock transfection, MIX30 or AG30 and analyzed for the induction of mutations 48 hrs post-treatment. Related data is shown in FIG. 12B.

AV16 and AV16 XPD-19-1 cells, which stably expressed XPD shRNA (FIG. 12B), were treated with a mock transfection, MIX30 or AG30 and analyzed for the induction of mutations 48 hrs post-treatment. We observed a mutation frequency ($45 \times 10^{-5}$) in XPD-proficient cells following AG30 treatment that was ~2-fold higher than the frequency obtained from MIX30 treated XPD+/+ cells ($20 \times 10^{-5}$) (Figure FIG. 8H). However, AG30 treatment ($95 \times 10^{-5}$) of XPD-deficient cells resulted in a 5-fold increase in mutation frequency compared to XPD-deficient cells that received MIX30 treatment ($19 \times 10^{-5}$) (FIG. 8H). The increase in mutation frequency observed in the XPD-deficient cells may be attributed in part to the cells inability to activate apoptosis. Taken together, these results position apoptosis as an important pathway in preserving genomic integrity in response to triplex-induced helical distortions.

DISCUSSION

Cells are faced with the fundamental decision of activating the appropriate ratio of DNA repair and apoptosis in response to damage. Data presented herein suggest that the TFIIH protein, XPD is involved in maintaining the balance between these two outcomes in response to the formation of altered helical structures. Thus, we provide evidence that the NER pathway is not only necessary for the repair of triplex structures, but is also important in the activation of pro-apoptotic pathways in response to helical distorting DNA structures. A key question exists as to how the cell determines when damage is excessive and how this determination triggers the shift from repair to apoptosis. The present study indicates that the absence of XPD results in a decrease in phosphorylation of the tyrosine 142 residue of H2AX in addition to p53. Recent work has determined that a balance between the kinase activity of WSTF and the phosphatase activity of Eya proteins help to regulate cellular fate following DNA damage (38,39). When repair is possible Y142 must be de-phosphorylated by Eya to allow for S139 phosphorylation and recruitment of repair proteins. Otherwise, Y142 phosphorylation persists causing the cell to activate apoptosis, thus eliminating the cells with irreversible damage.

Although studies indicate that Y142 is gradually de-phosphorylated after DNA damage, it is possible that Y142 is re-phosphorylated after futile attempts to repair the excessive DNA damage in order to facilitate apoptosis. It is theoretically possible that if XPD is not present to trigger the switch to activate apoptosis, this re-phosphorylation does not take place and the remaining DNA damage response proteins necessary for apoptosis are not recruited. Chymkowitch et al have recently shown that the TFIIH complex is able to phosphorylate the androgen receptor at position AR/S515 via cdk7 (42). Additionally, mutations in the C-terminal domain of XPD were found to disturb the architecture of TFIIH leading to the dysregulation of cdk7-related phosphorylation (43,44). Taken together, these findings along with our result that XPD co-localizes with γH2AX provide support for an XPD-dependent apoptotic pathway.

The XPD protein has been identified as having a role in NER, transcription and possibly cell cycle. However, XPD also exists in non-TFIIH complexes, such as CAK-XPD and MMXD and has function in other cellular processes, including apoptosis. Knockdown of XPD did not reduce the intensity of triplex-induced DSBs or γH2AX foci formation, although a significant decrease in apoptosis was observed. It is apparent from the work presented that key proteins, which contribute to cellular survival through their involvement in DNA repair, also participate in the mechanism that shifts the cell from DNA repair to apoptosis.

Intramolecular triplex DNA structures exist transiently in genomic DNA and represent an endogenous source of genomic instability. Naturally occurring sequences capable of forming H-DNA are typically located in promoters and exons and are believed to be involved in the regulation of expression of several disease-linked genes (45-48). The human c-myc gene, which is often translocated and over-expressed in tumors, contains an H-DNA forming sequence in its promoter (45). Many breakpoints on the translocated c-myc gene are clustered around the H-DNA forming sequence in the promoter region in Burkitt's lymphoma (14). Studies suggest that non-canonical structures result in fragile sites or mutation hotspots, and can lead to double strand breaks (DSBs) and subsequent translocation of the gene. The maintenance of a mechanism by which the cell can actively determine cellular fate in response to the formation of these structures may be of central importance for avoiding progression to cancer, because the default mechanism of apoptosis prevents expansion of cells in which unrepaired damage would lead to mutation and to carcinogenesis. Additionally, XPD may be an integral component in determining the fate of cells assaulted by other NER-recognized DNA damage including those induced by UV. Work described herein highlights the complexity of the balance between DNA repair and apoptosis in response to damage induced by altered helical structures.

Example 3

Triplex-Induced Apoptosis in Breast Cancer

Figure 13:
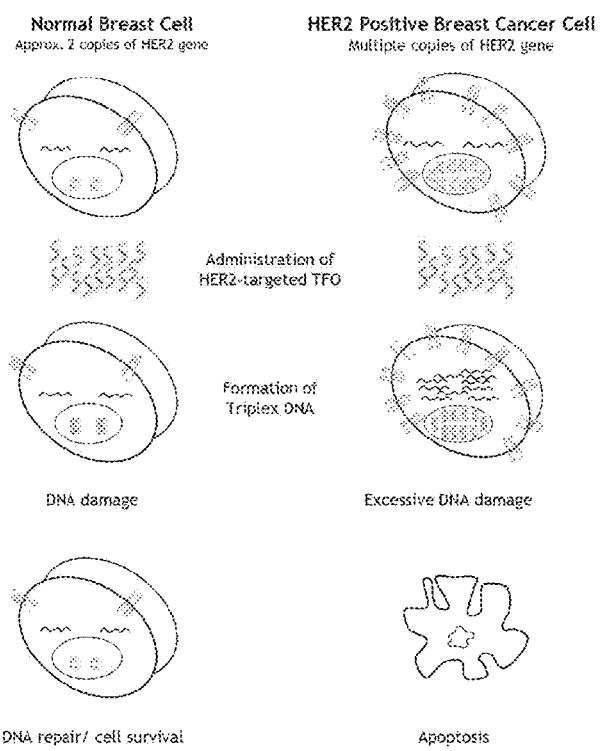
FIG. 13. Schematic of therapeutic strategy to use gene-targeted apoptosis as a treatment for HER2-positive breast cancer. Triplex DNA formed at chromosomal sites by exogenous triplex-forming oligonucleotides (TFOs) can induce apoptosis in human cells. However, induction of apoptosis only occurs in response to the formation of multiple triplex structures; not just one or two, since the nucleotide excision repair (NER) pathway is capable of efficiently repairing a low level of damage. The amplification of the HER2 gene seen in approximately 30% of breast cancers provides an opportunity to use TFOs to create multiple apoptosis inducing triplexes specifically in the cancer cells and not in healthy cells, which lack HER2 gene amplification.
Figure 16:
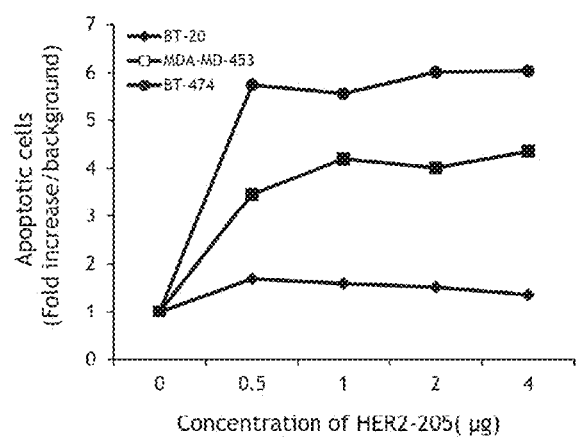
FIG. 16. Dose response of triplex-induced apoptosis. Dose response of increasing concentrations of HER2-205 and its effect of apoptotic cell death in three breast cancer cells lines. BT20 (null), MDA-MD-453 (11 copies of HER2), and BT-474 (52 copies).

The threshold for triplex-induced apoptosis in vivo can be determined using known methods and the molecular mechanisms responsible for the anticancer activity of HER2-targeted TFOs was characterized (FIG. 13). Susceptibility of HER2-positive breast cancer cells to gene-targeted apoptosis was determined using cell lines with varying HER2 gene copy number, including BT-20, MDA-MB-453, SKBR3, BT-474 HER2-positive cell lines (FIGS. 14A and 14B). As shown in FIGS. 15A-15C, the amount of triplex induced apoptosis increased as the HER2 gene copy number increased. The dose response of increasing concentrations of the TFM, HER2-205 and the induced apoptosis in HER2 positive breast cancer cells was also evaluated (FIG. 16).

Figure 18:
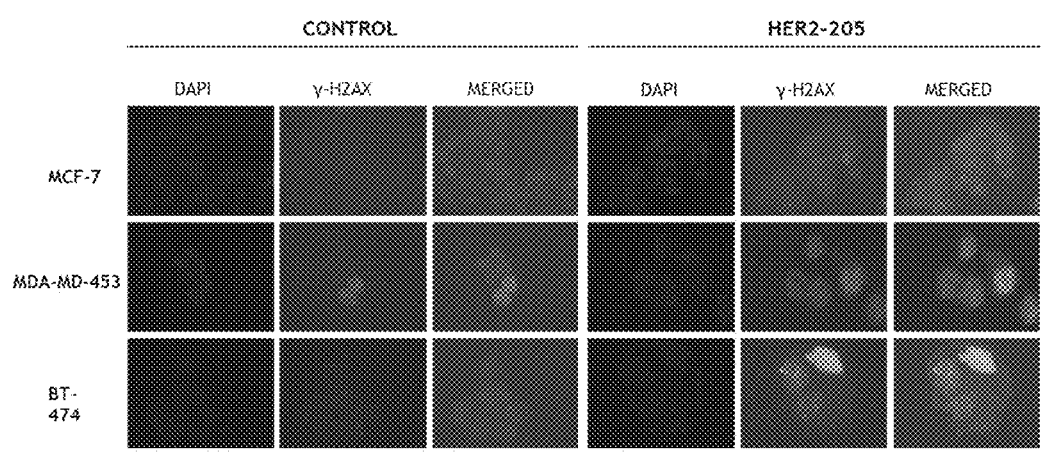
FIG. 18. Immunofluorescence of triplex-induced γH2AX foci following treatment with HER2-205. HER2-targeted TFOs specifically induce γH2AX foci in HER2 overexpressing breast cancer cells.
Figure 19:
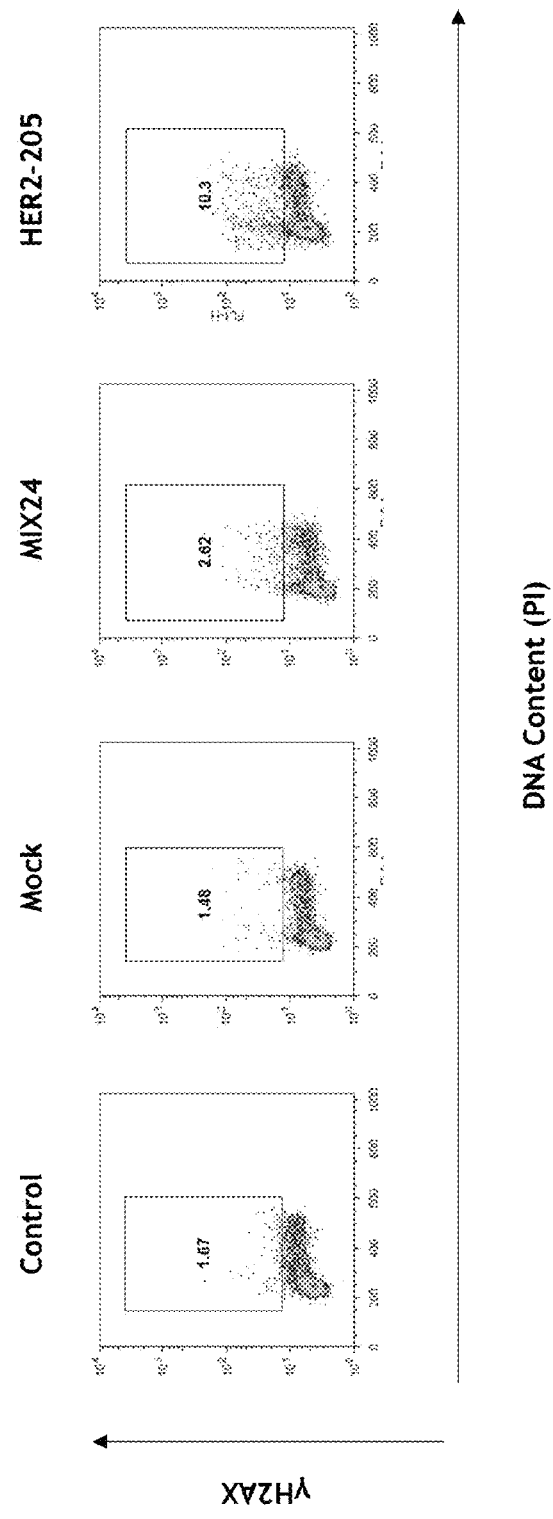
FIG. 19. HER2-targeted TFOs induce cell cycle independent γH2AX. Flow cytometry profiles of BT-474 cells stained for expression of γH2AX and propidium iodide (PI) to measure DNA content and identify phases of the cell cycle. Cells were treated with HER2-205. The box indicates the gate for high levels of γH2AX and number represent percentage of cells with high levels of γH2AX.

The mechanisms involved in triplex-induced apoptosis were also assessed, with emphasis on DNA damage recognition and response pathways (FIGS. 17-19). Results provided herein support the conclusion that the mechanisms involved are independent of HER2 cellular function and only dependent on HER2 gene amplification.

The therapeutic efficacy of HER2-targeted TFOs to specifically suppress the growth and metastasis of HER2-positive breast tumors in vivo was also assessed by evaluating the antitumor activity of HER2-targeted TFOs in an athymic nude mouse model for HER2-positive breast cancer (FIG. 20A). As shown in FIG. 20B, the mice that received the triplex inducing treatment (HER2-205) had a lower tumor burden (volume) as compared to the mice that received vehicle only.

Example 4

Triplex Induced Apoptosis in Chemotherapeutic-Resistant Cancers

Figure 22:
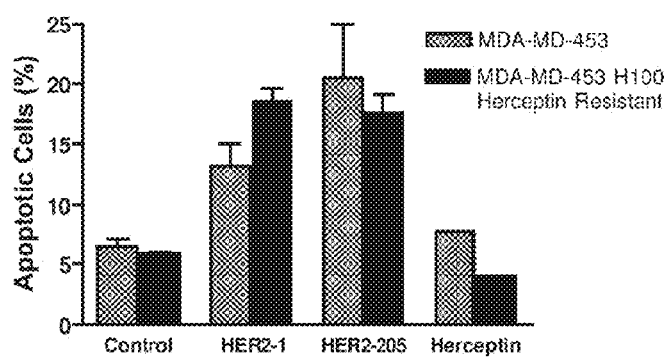
FIG. 22 shows results of assessment of gene-targeted apoptosis for treating Herceptin-resistant breast cancer.

Herceptin-resistance can be attributed in part to the activation of aberrant signaling pathways that compensate for the inhibition of HER2 cellular growth activity. Targeted drugs that utilize a mechanism of action that is independent of HER2 cellular function may avoid this form of acquired resistance. The feasibility of using gene-targeted apoptosis as a treatment strategy for Herceptin-resistant breast cancers is further assessed, for example, by testing the ability of the biologically active HER2-targeted TFOs to inhibit cell growth and induce apoptosis in Herceptin-resistant breast cancer cells. As shown in FIG. 22, treatment with the HER2-targeting TFOs resulted in similar levels of induced apoptosis in both the Herceptin-sensitive and resistant cells.

Example 5

Triplex Induced Apoptosis in Ovarian Cancer Cells

Figure 21:
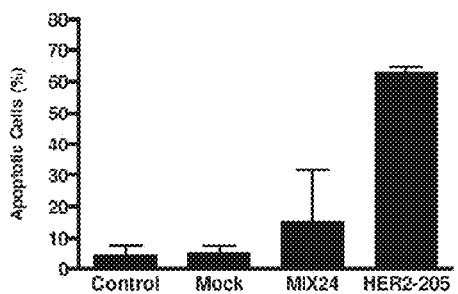
FIG. 21. Gene-targeted apoptosis in a HER2 positive ovarian cancer cell line. Cells were treated with the triplex forming oligonucleotide HER2-205 or the control oligonucleotide MIX24 and assessed for apoptosis.

Susceptibility of HER2-positive ovarian cancer cells to gene-targeted apoptosis was determined using ovarian cancer cell lines. The cells were treated with the triplex forming oligonucleotide HER2-205 or the control oligonucleotide MIX24 and assessed for the induction of apoptosis. As shown in FIG. 21, treatment with the HER2-targeting TFO resulted in apoptosis of more than 60% of cells as compared to approximately 15% of cells that were treated with the control oligonucleotide. These results indicate that triplex forming oligonucleotides can be used to induce apoptosis in other cancer cell types in addition to breast cancer cells.

REFERENCES

1. Bernstein, C., Bernstein, H., Payne, C. M. and Garewal, H. (2002) DNA repair/pro-apoptotic dual-role proteins in five major DNA repair pathways: fail-safe protection against carcinogenesis. *Mutation research,* 511, 145-178.
2. de Laat, W. L., Jaspers, N. G. and Hoeijmakers, J. H. (1999) Molecular mechanism of nucleotide excision repair. *Genes & development,* 13, 768-785.
3. Wang, X. W., Vermeulen, W., Coursen, J. D., Gibson, M., Lupold, S. E., Forrester, K., Xu, G., Elmore, L., Yeh, H., Hoeijmakers, J. H. et al. (1996) The XPB and XPD DNA helicases are components of the p53-mediated apoptosis pathway. *Genes & development,* 10, 1219-1232.
4. Robles, A. I., Wang, X. W. and Harris, C. C. (1999) Drug-induced apoptosis is delayed and reduced in XPD lymphoblastoid cell lines: possible role of TFIIH in p53-mediated apoptotic cell death. *Oncogene,* 18, 4681-4688.
5. Wang, X. W., Yeh, H., Schaeffer, L., Roy, R., Moncollin, V., Egly, J. M., Wang, Z., Freidberg, E. C., Evans, M. K., Taffe, B. G. et al. (1995) p53 modulation of TFIIH-associated nucleotide excision repair activity. *Nature genetics,* 10, 188-195.
6. Wang, G., Seidman, M. M. and Glazer, P. M. (1996) Mutagenesis in mammalian cells induced by triple helix formation and transcription-coupled repair. *Science* (New York,
N. Y, 271, 802-805.
7. Rogers, F. A., Vasquez, K. M., Egholm, M. and Glazer, P. M. (2002) Site-directed recombination via bifunctional PNA-DNA conjugates. *Proceedings of the National Academy of Sciences of the United States of America*, 99, 16695-16700.
8. Watson, J. D. and Crick, F. H. (1974) Molecular structure of nucleic acids: a structure for deoxyribose nucleic acid. J. D. Watson and F. H. C. Crick. Published in Nature, number 4356 Apr. 25, 1953. *Nature*, 248, 765.
9. Htun, H. and Dahlberg, J. E. (1988) Single strands, triple strands, and kinks in H-DNA. *Science (New York, N. Y*, 241, 1791-1796.
10. Voloshin, O. N., Mirkin, S. M., Lyamichev, V. I., Belotserkovskii, B. P. and Frank-Kamenetskii, M. D. (1988) Chemical probing of homopurine-homopyrimidine mirror repeats in supercoiled DNA. *Nature*, 333, 475-476.
11. Mirkin, S. M., Lyamichev, V. I., Drushlyak, K. N., Dobrynin, V. N., Filippov, S. A. and Frank-Kamenetskii, M. D. (1987) DNA H form requires a homopurine-homopyrimidine mirror repeat. *Nature*, 330, 495-497.
12. Schroth, G. P. and Ho, P. S. (1995) Occurrence of potential cruciform and H-DNA forming sequences in genomic DNA. *Nucleic acids research*, 23, 1977-1983.
13. Wang, G. and Vasquez, K. M. (2004) Naturally occurring H-DNA-forming sequences are mutagenic in mammalian cells. *Proceedings of the National Academy of Sciences of the United States of America*, 101, 13448-13453.
14. Saglio, G., Grazia Borrello, M., Guerrasio, A., Sozzi, G., Serra, A., di Celle, P. F., Foa, R., Ferrarini, M., Roncella, S., Borgna Pignatti, C. et al. (1993) Preferential clustering of chromosomal breakpoints in Burkitt's lymphomas and L3 type acute lymphoblastic leukemias with a t(8;14) translocation. *Genes, chromosomes & cancer*, 8, 1-7.
15. Knauert, M. P., Lloyd, J. A., Rogers, F. A., Datta, H. J., Bennett, M. L., Weeks, D. L. and Glazer, P. M. (2005) Distance and affinity dependence of triplex-induced recombination. *Biochemistry*, 44, 3856-3864.
16. Rogers, F. A., Manoharan, M., Rabinovitch, P., Ward, D. C. and Glazer, P. M. (2004) Peptide conjugates for chromosomal gene targeting by triplex-forming oligonucleotides. *Nucleic acids research*, 32, 6595-6604.
17. Stachelek, G. C., Dalal, S., Donigan, K. A., Campisi Hegan, D., Sweasy, J. B. and Glazer, P. M. Potentiation of temozolomide cytotoxicity by inhibition of DNA polymerase beta is accentuated by BRCA2 mutation. *Cancer research*, 70, 409-417.
18. Rogers, F. A., Lin, S. S., Hegan, D. C., Krause, D. S. and Glazer, P. M. (2012) Targeted gene modification of hematopoietic progenitor cells in mice following systemic administration of a PNA-peptide conjugate. *Molecular therapy: the journal of the American Society of Gene Therapy*, 20, 109-118.
19. Gunther, E. J., Yeasky, T. M., Gasparro, F. P. and Glazer, P. M. (1995) Mutagenesis by 8-methoxypsoralen and 5-methylangelicin photoadducts in mouse fibroblasts: mutations at cross-linkable sites induced by offoadducts as well as cross-links. *Cancer research*, 55, 1283-1288.
20. Wang, G., Chen, Z., Zhang, S., Wilson, G. L. and Jing, K. (2001) Detection and determination of oligonucleotide triplex formation-mediated transcription-coupled DNA repair in HeLa nuclear extracts. *Nucleic acids research*, 29, 1801-1807.
21. Macris, M. A. and Glazer, P. M. (2003) Transcription dependence of chromosomal gene targeting by triplex-forming oligonucleotides. *The Journal of biological chemistry*, 278, 3357-3362.
22. Johnson, M. D., 3rd and Fresco, J. R. (1999) Third-strand in situ hybridization (TISH) to non-denatured metaphase spreads and interphase nuclei. *Chromosoma*, 108, 181-189.
23. Schwartz, T. R., Vasta, C. A., Bauer, T. L., Parekh-Olmedo, H. and Kmiec, E. B. (2008) G-rich oligonucleotides alter cell cycle progression and induce apoptosis specifically in OE19 esophageal tumor cells. *Oligonucleotides*, 18, 51-63.
24. Qi, H., Lin, C. P., Fu, X., Wood, L. M., Liu, A. A., Tsai, Y. C., Chen, Y., Barbieri, C. M., Pilch, D. S. and Liu, L. F. (2006) G-quadruplexes induce apoptosis in tumor cells. *Cancer research*, 66, 11808-11816.
25. Do, N. Q., Lim, K. W., Teo, M. H., Heddi, B. and Phan, A. T. (2011) Stacking of G-quadruplexes: NMR structure of a G-rich oligonucleotide with potential anti-HIV and anticancer activity. *Nucleic acids research*, 39, 9448-9457.
26. Kutyavin, I. V., Lokhov, S. G., Afonina, I. A., Dempcy, R., Gall, A. A., Gorn, V. V., Lukhtanov, E., Metcalf, M., Mills, A., Reed, M. W. et al. (2002) Reduced aggregation and improved specificity of G-rich oligodeoxyribonucleotides containing pyrazolo[3,4-d]pyrimidine guanine bases. *Nucleic acids research*, 30, 4952-4959.
27. Shah, G. M., Shah, R. G. and Poirier, G. G. (1996) Different cleavage pattern for poly(ADP-ribose) polymerase during necrosis and apoptosis in HL-60 cells. *Biochemical and biophysical research communications*, 229, 838-844.
28. Rogakou, E. P., Pilch, D. R., Orr, A. H., Ivanova, V. S. and Bonner, W. M. (1998) DNA double-stranded breaks induce histone H2AX phosphorylation on serine 139. *The Journal of biological chemistry*, 273, 5858-5868.
29. Fernandez-Capetillo, O., Lee, A., Nussenzweig, M. and Nussenzweig, A. (2004) H2AX: the histone guardian of the genome. *DNA repair*, 3, 959-967.
30. Huang, X., Okafuji, M., Traganos, F., Luther, E., Holden, E. and Darzynkiewicz, Z. (2004) Assessment of histone H2AX phosphorylation induced by DNA topoisomerase I and II inhibitors topotecan and mitoxantrone and by the DNA cross-linking agent cisplatin. *Cytometry. Part A: the journal of the International Society for Analytical Cytology*, 58, 99-110.
31. Cleaver, J. E. (2011) gammaH2Ax: biomarker of damage or functional participant in DNA repair "all that glitters is not gold!". *Photochemistry and photobiology*, 87, 1230-1239.
32. Huang, X., Halicka, H. D., Traganos, F., Tanaka, T., Kurose, A. and Darzynkiewicz, Z. (2005) Cytometric assessment of DNA damage in relation to cell cycle phase and apoptosis. *Cell proliferation*, 38, 223-243.
33. Batty, D. P. and Wood, R. D. (2000) Damage recognition in nucleotide excision repair of DNA. *Gene*, 241, 193-204.
34. de Boer, J., Donker, I., de Wit, J., Hoeijmakers, J. H. and Weeda, G. (1998) Disruption of the mouse xeroderma pigmentosum group D DNA repair/basal transcription gene results in preimplantation lethality. *Cancer research*, 58, 89-94.
35. Kapoor, M., Hamm, R., Yan, W., Taya, Y. and Lozano, G. (2000) Cooperative phosphorylation at multiple sites is required to activate p53 in response to UV radiation. *Oncogene*, 19, 358-364.
36. Shieh, S. Y., Ikeda, M., Taya, Y. and Prives, C. (1997) DNA damage-induced phosphorylation of p53 alleviates inhibition by MDM2. *Cell*, 91, 325-334.

37. Steegenga, W. T., van der Eb, A. J. and Jochemsen, A. G. (1996) How phosphorylation regulates the activity of p53. *Journal of molecular biology*, 263, 103-113.
38. Xiao, A., Li, H., Shechter, D., Ahn, S. H., Fabrizio, L. A., Erdjument-Bromage, H., Ishibe-Murakami, S., Wang, B., Tempst, P., Hofmann, K. et al. (2009) WSTF regulates the H2A.X DNA damage response via a novel tyrosine kinase activity. *Nature*, 457, 57-62.
39. Cook, P. J., Ju, B. G., Telese, F., Wang, X., Glass, C. K. and Rosenfeld, M. G. (2009) Tyrosine dephosphorylation of H2AX modulates apoptosis and survival decisions. *Nature*, 458, 591-596.
40. Vasquez, K. M., Narayanan, L. and Glazer, P. M. (2000) Specific mutations induced by triplex-forming oligonucleotides in mice. *Science* (New York, N. Y, 290, 530-533.
41. Vasquez, K. M., Wang, G., Havre, P. A. and Glazer, P. M. (1999) Chromosomal mutations induced by triplex-forming oligonucleotides in mammalian cells. *Nucleic acids research*, 27, 1176-1181.
42. Chymkowitch, P., Le May, N., Charneau, P., Compe, E. and Egly, J. M. The phosphorylation of the androgen receptor by TFIIH directs the ubiquitin/proteasome process. *The EMBO journal*, 30, 468-479.
43. Keriel, A., Stary, A., Sarasin, A., Rochette-Egly, C. and Egly, J. M. (2002) XPD mutations prevent TFIIH-dependent transactivation by nuclear receptors and phosphorylation of RARalpha. *Cell*, 109, 125-135.
44. Compe, E., Drane, P., Laurent, C., Diderich, K., Braun, C., Hoeijmakers, J. H. and Egly, J. M. (2005) Dysregulation of the peroxisome proliferator-activated receptor target genes by XPD mutations. *Molecular and cellular biology*, 25, 6065-6076.
45. Kinniburgh, A. J. (1989) A cis-acting transcription element of the c-myc gene can assume an H-DNA conformation. *Nucleic acids research*, 17, 7771-7778.
46. Pestov, D. G., Dayn, A., Siyanova, E., George, D. L. and Mirkin, S. M. (1991) H-DNA and Z-DNA in the mouse c-Ki-ras promoter. *Nucleic acids research*, 19, 6527-6532.
47. Bacolla, A., Jaworski, A., Connors, T. D. and Wells, R. D. (2001) Pkd1 unusual DNA conformations are recognized by nucleotide excision repair. *The Journal of biological chemistry*, 276, 18597-18604.
48. Belotserkovskii, B. P., De Silva, E., Tornaletti, S., Wang, G., Vasquez, K. M. and Hanawalt, P. C. (2007) A triplex-forming sequence from the human c-MYC promoter interferes with DNA transcription. *The Journal of biological chemistry*, 282, 32433-32441.

What is claimed is:

1. A method of inducing apoptosis in breast cancer cells in which the HER2 gene is amplified, the method comprising contacting breast cancer cells in which the HER2 gene is amplified with
   (a) triplex inducing oligonucleotides (TFOs) specific for a polypurine site in the amplified HER2 gene and (b) a transport peptide, under conditions under which the TFOs and the transport peptide enter the breast cancer cells and the TFOs enter the breast cancer cells in sufficient quantity to induce apoptosis.

2. A method of inducing apoptosis in breast cancer cells comprising an amplified HER2 gene, the method comprising contacting breast cancer cells comprising an amplified HER2 gene with
   (a) triplex forming oligonucleotides (TFOs), specific for a polypurine site in the amplified HER2 gene and (b) a transport peptide, under conditions under which the TFOs and the transport peptides enter the breast cancer cells comprising amplified HER2 gene and TFOs enter the breast cancer cells comprising amplified HER2 gene in sufficient quantity, bind multiple polypurine site(s) in the amplified HER2 gene and form multiple triplexes in the cells and induce apoptosis.

3. The method of claim 1, wherein the TFOs and the transport peptides are linked, either covalently or non-covalently.

4. The method of claim 1, wherein the TFOs and the transport peptides are not linked and are contacted with the breast cancer cells as a mixture.

5. The method of claim 1, wherein the breast cancer cells in which the HER2 gene is amplified are resistant to Herceptin.

6. The method of claim 2, wherein the TFOs and the transport peptides are linked, either covalently or non-covalently.

7. The method of claim 2, wherein the TFOs and the transport peptides are not linked and are contacted with the breast cancer cells as a mixture.

8. The method of claim 2, wherein the breast cancer cells comprising an amplified HER2 gene are resistant to Herceptin.

9. The method of claim 1, wherein the TFOs comprise 5'GAGGAGGAGTGGGAGAATGGGGGG (SEQ ID NO: 16).

10. The method of claim 9, wherein the transport peptide comprises a cationic cell-penetrating peptide.

11. The method of claim 1, wherein the TFOs comprise 5'GAGGAGGAGTGGGAGAATGGGGGG (SEQ ID NO: 16) and the transport peptide comprises a peptide selected from the group consisting of: Penetratin or Antenapedia (RQIKIWFQNRRMKWKK (SEQ ID NO: 1), PTD RQIKWFQNRRMKWKK (SEQ ID NO: 2); HIV TAT protein (YGRKKRRQRRR (SEQ ID NO: 3); SynB1 (RGGRLSYSRRRFSTSTGR (SEQ ID NO: 4); SynB3 (RRLSYSRRRF (SEQ ID NO: 5); PTD-4 (PIRRRKKLRRLK (SEQ ID NO: 6); PTD-5 (RRQRRTSKLMKR (SEQ ID NO: 7); FHV Coat-(35-49) (RRRRNRTRRNRRRVR (SEQ ID NO: 8); BMV Gag-(7-25) (KMTRAQRRAAARRNRWTAR (SEQ ID NO: 9); HTLV-II Rex-(4-16) (TRRQRTRRARRNR (SEQ ID NO: 10); D-Tat (GRKKRRQRRRPPQ (SEQ ID NO: 11); and R9-Tat (GRRRRRRRRRPPQ (SEQ ID NO: 12).

12. The method of claim 2, wherein the TFOs comprise 5'GAGGAGGAGTGGGAGAATGGGGGG (SEQ ID NO: 16).

13. The method of claim 12, wherein the transport peptide comprises a cationic cell-penetrating peptide.

14. The method of claim 2, wherein the TFOs comprise: 5'GAGGAGGAGTGGGAGAATGGGGGG (SEQ ID NO: 16 and the transport peptide comprises a peptide selected from the group consisting of: Penetratin or Antenapedia (RQIKIWFQNRRMKWKK (SEQ ID NO: 1), PTD RQIKWFQNRRMKWKK (SEQ ID NO: 2); HIV TAT protein (YGRKKRRQRRR (SEQ ID NO: 3); SynB1 (RGGRLSYSRRRFSTSTGR (SEQ ID NO: 4); SynB3 (RRLSYSRRRF (SEQ ID NO: 5); PTD-4 (PIRRRKKLRRLK (SEQ ID NO: 6); PTD-5 (RRQRRTSKLMKR (SEQ ID NO: 7); FHV Coat-(35-49) (RRRRNRTRRNRRRVR (SEQ ID NO: 8); BMV Gag-(7-25) (KMTRAQRRAAARRNRWTAR (SEQ ID NO: 9); HTLV-II Rex-(4-16) (TRRQRTRRARRNR (SEQ ID NO: 10); D-Tat (GRKKRRQRRRPPQ (SEQ ID NO: 11); and R9-Tat (GRRRRRRRRRPPQ (SEQ ID NO: 12).

* * * * *

UNITED STATES PATENT AND TRADEMARK OFFICE
CERTIFICATE OF CORRECTION

PATENT NO. : 9,587,238 B1
APPLICATION NO. : 14/335371
DATED : March 7, 2017
INVENTOR(S) : Faye A. Rogers It is certified that error appears in the above-identified patent and that said Letters Patent is hereby corrected as shown below:

In the Specification

Column 1, Line 3 insert:
--This invention was made with government support under CA120049 and CA185192 awarded by National Institutes of Health. The government has certain rights in the invention.--

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*